US010778944B2

(12) United States Patent
Hilkes et al.

(10) Patent No.: US 10,778,944 B2
(45) Date of Patent: Sep. 15, 2020

(54) APPARATUS AND METHOD FOR ENHANCING HUMAN VISUAL PERFORMANCE IN A HEAD WORN VIDEO SYSTEM

(71) Applicant: eSIGHT CORP., Kanata (CA)

(72) Inventors: Robert Hilkes, Ottawa (CA); Frank Jones, Carp (CA); Kevin Rankin, Kanata (CA)

(73) Assignee: eSight Corp., Kanata, Ontario (CA)

(*) Notice: Subject to any disclaimer, the term of this patent is extended or adjusted under 35 U.S.C. 154(b) by 0 days.

(21) Appl. No.: 16/291,416

(22) Filed: Mar. 4, 2019

(65) Prior Publication Data
US 2019/0199974 A1 Jun. 27, 2019

Related U.S. Application Data

(63) Continuation of application No. 15/361,185, filed on Nov. 25, 2016, now Pat. No. 10,225,526, which is a (Continued)

(51) Int. Cl.
H04N 7/18 (2006.01)
H04N 13/178 (2018.01)
(Continued)

(52) U.S. Cl.
CPC ............ *H04N 7/185* (2013.01); *A61H 3/061* (2013.01); *G02B 3/12* (2013.01); *G02B 27/017* (2013.01); *G02B 27/0172* (2013.01); *G06F 3/013* (2013.01); *G06T 11/00* (2013.01); *G09B 21/008* (2013.01); *H04N 13/178* (2018.05); *A61F 9/08* (2013.01); *A61H 2201/1604* (2013.01);
(Continued)

(58) Field of Classification Search
None
See application file for complete search history.

(56) References Cited

U.S. PATENT DOCUMENTS 5,583,566 A * 12/1996 Kanno ................ G11B 27/105
348/72
5,614,943 A * 3/1997 Nakamura ......... A61B 1/00105
348/72

(Continued)

Primary Examiner — Talha M Nawaz
(74) Attorney, Agent, or Firm — Rosenberg, Klein & Lee

(57) ABSTRACT

Visual impairment, or vision impairment, refers to the vision loss of an individual to such a degree as to require additional support for one or more aspects of their life. Such a significant limitation of visual capability may result from disease, trauma, congenital, and/or degenerative conditions that cannot be corrected by conventional means, such as refractive correction, such as eyeglasses or contact lenses, medication, or surgery. According to embodiments of the invention a method of augmenting a user's sight is provided comprising obtaining an image of a scene using a camera carried by the individual, transmitting the obtained image to a processor, selecting an algorithm of a plurality of spectral, spatial, and temporal image modification algorithms to be applied to the image by the processor, modifying the image using the algorithm substantially in real time, and displaying the modified image on a display device worn by the individual.

24 Claims, 18 Drawing Sheets

Related U.S. Application Data continuation of application No. 13/916,806, filed on Jun. 13, 2013, now Pat. No. 9,516,283, and a continuation of application No. 13/769,353, filed on Feb. 17, 2013, now abandoned.

(60) Provisional application No. 61/659,128, filed on Jun. 13, 2012, provisional application No. 61/599,996, filed on Feb. 17, 2012.

(51) Int. Cl.
*G06F 3/01* (2006.01)
*G09B 21/00* (2006.01)
*A61H 3/06* (2006.01)
*G06T 11/00* (2006.01)
*G02B 27/01* (2006.01)
*G02B 3/12* (2006.01)
*A61F 9/08* (2006.01)
*H04N 13/332* (2018.01)

(52) U.S. Cl.
CPC .. *A61H 2201/165* (2013.01); *A61H 2201/501* (2013.01); *A61H 2201/5007* (2013.01); *A61H 2201/5092* (2013.01); *A61H 2201/5097* (2013.01); *G02B 2027/011* (2013.01); *G02B 2027/014* (2013.01); *G02B 2027/0138* (2013.01); *G02B 2027/0178* (2013.01); *H04N 13/332* (2018.05)

(56) References Cited

U.S. PATENT DOCUMENTS

| | | | | |
|---|---|---|---|---|
| 10,387,720 | B2* | 8/2019 | Johnson | G06K 9/00711 |
| 2004/0009459 | A1* | 1/2004 | Anderson | G06T 19/00 |
| | | | | 434/262 |
| 2007/0287124 | A1* | 12/2007 | Yamamoto | G09B 23/28 |
| | | | | 433/55 |
| 2012/0026308 | A1* | 2/2012 | Johnson | G06T 7/73 |
| | | | | 348/77 |
| 2014/0087342 | A1* | 3/2014 | Campanatti, Jr. | G09B 23/00 |
| | | | | 434/262 |

* cited by examiner

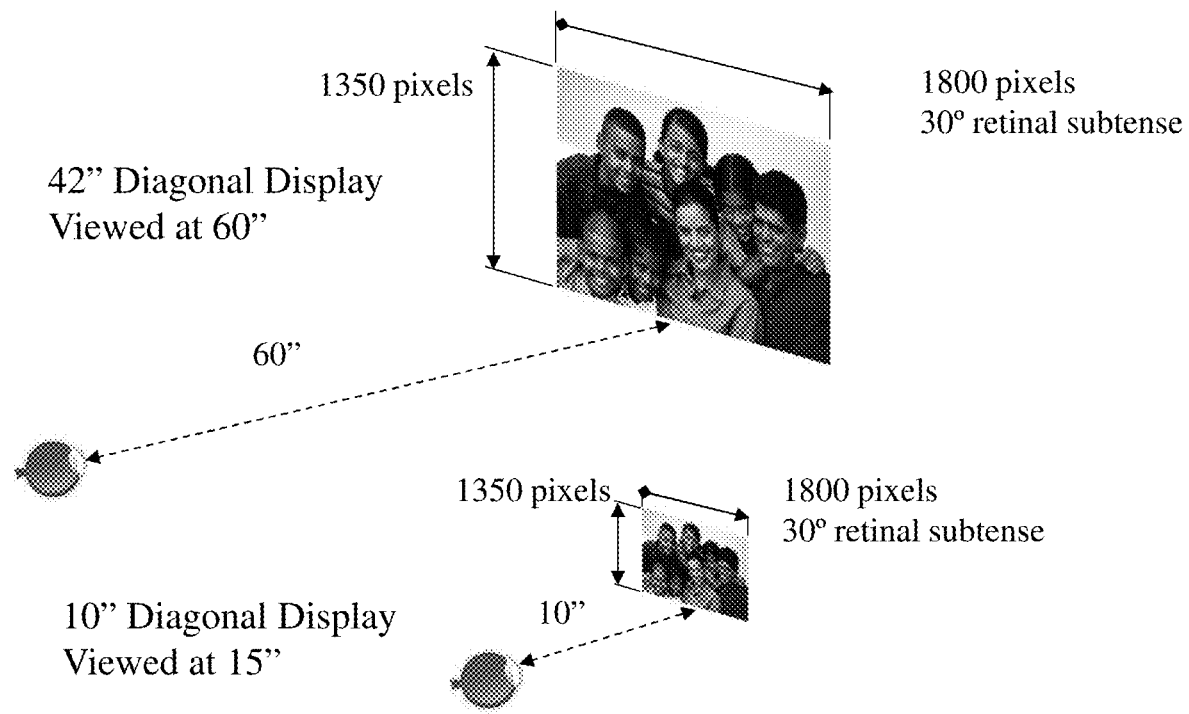
Figure 3B
Figure 3C
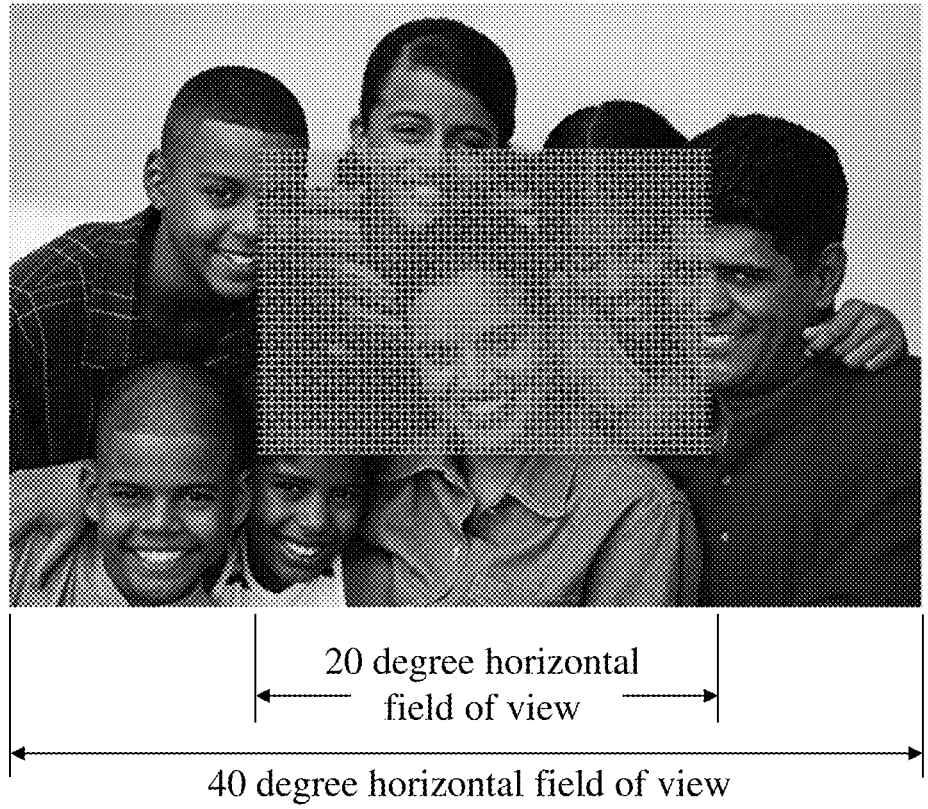

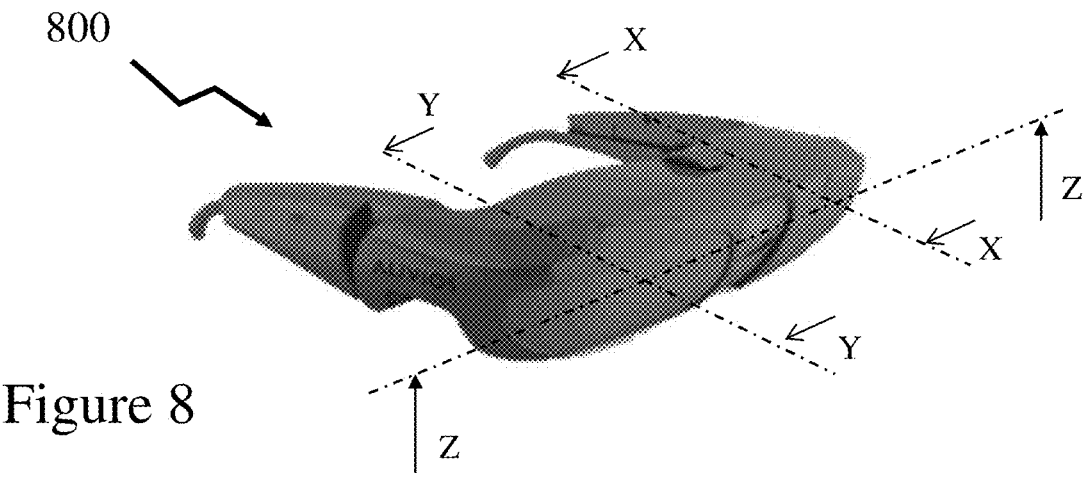
Figure 8
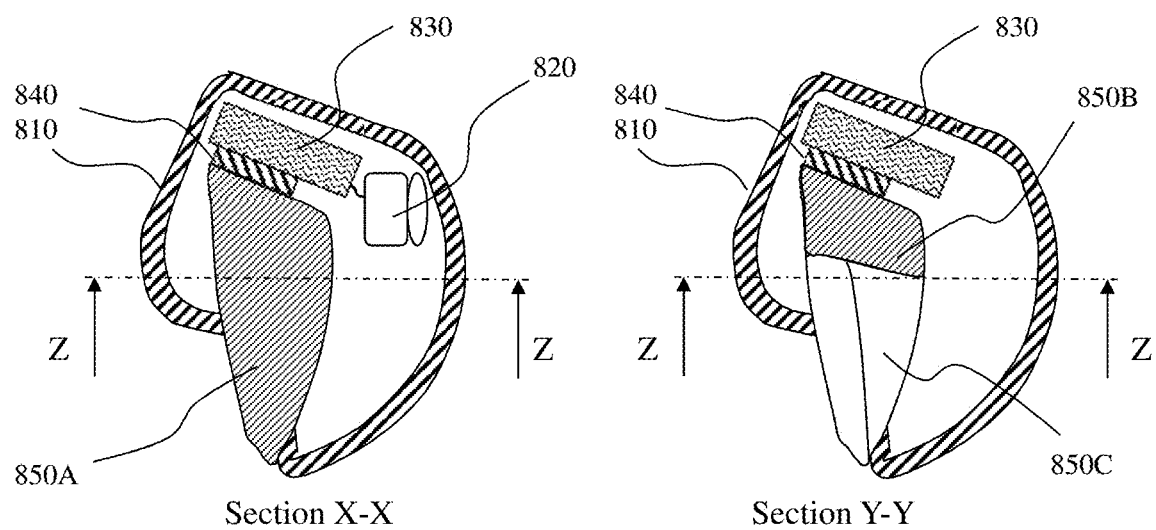
Section X-X    Section Y-Y
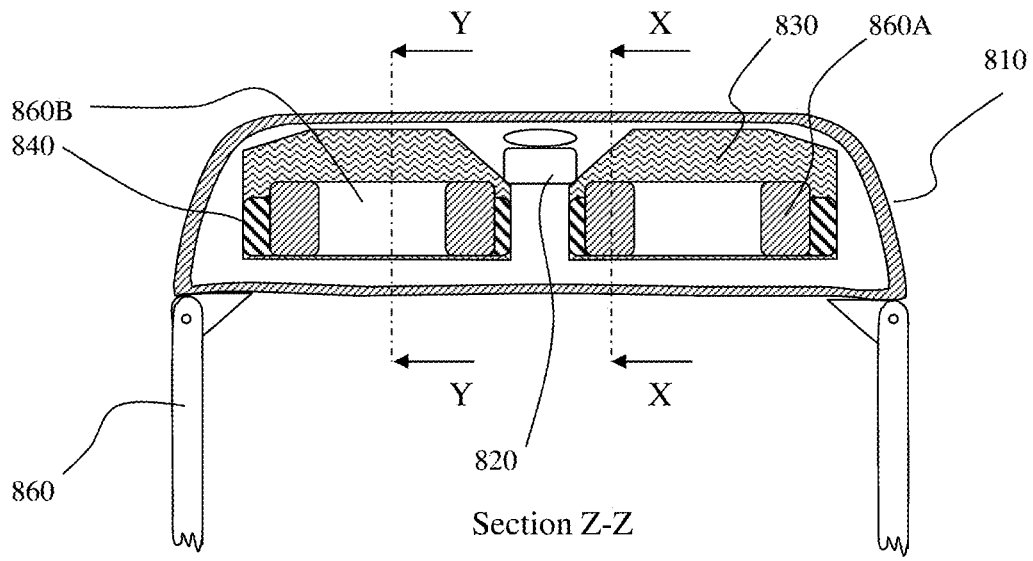
Section Z-Z

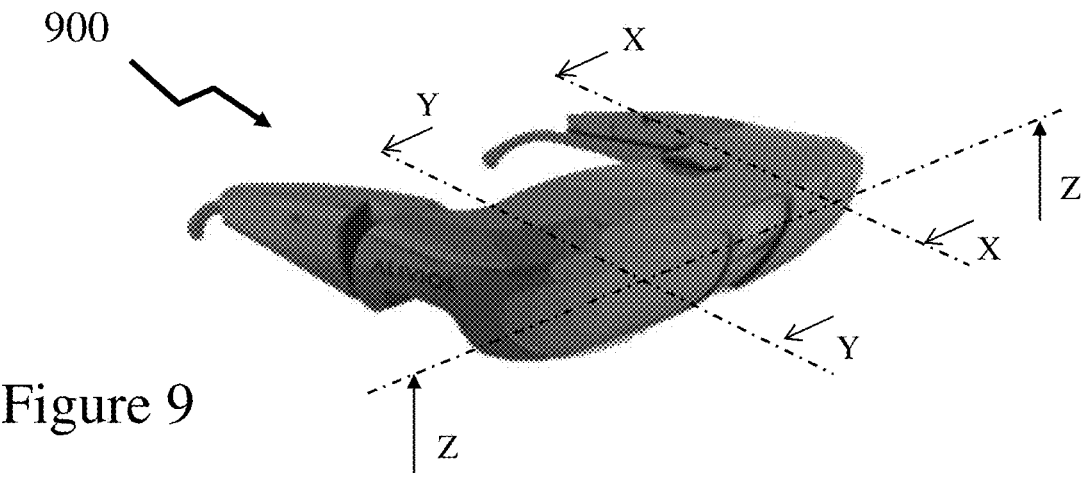
Figure 9
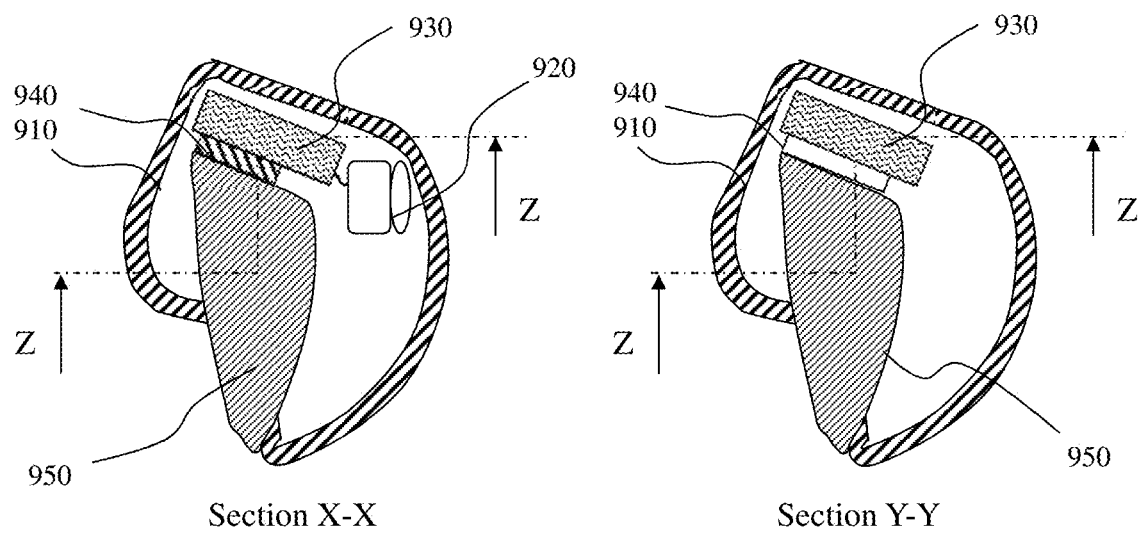
Section X-X    Section Y-Y
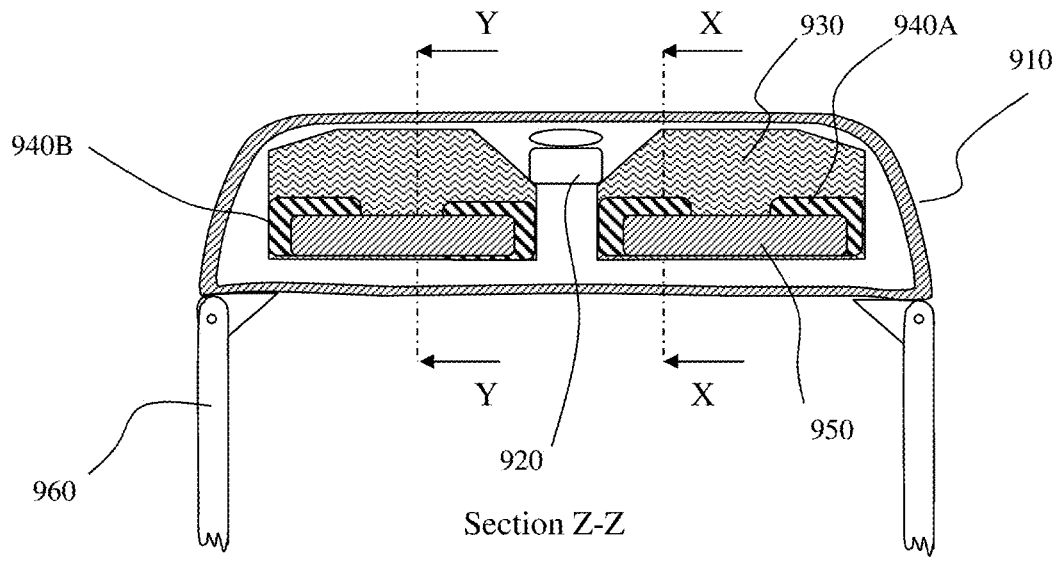
Section Z-Z

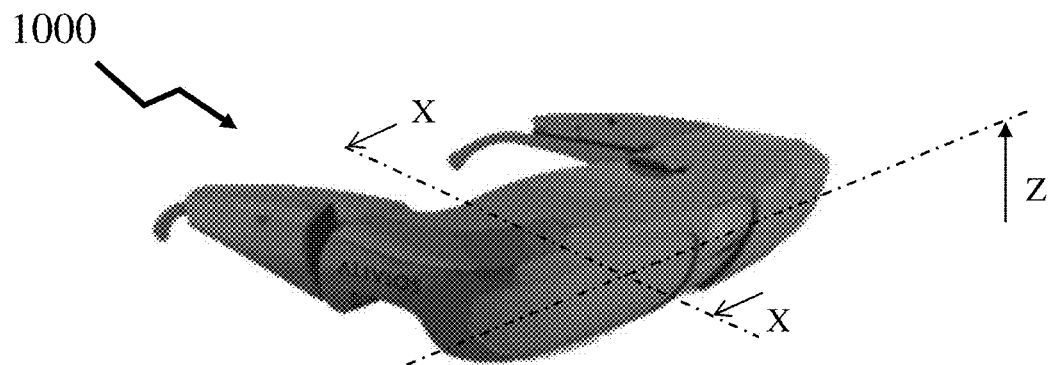
Figure 10
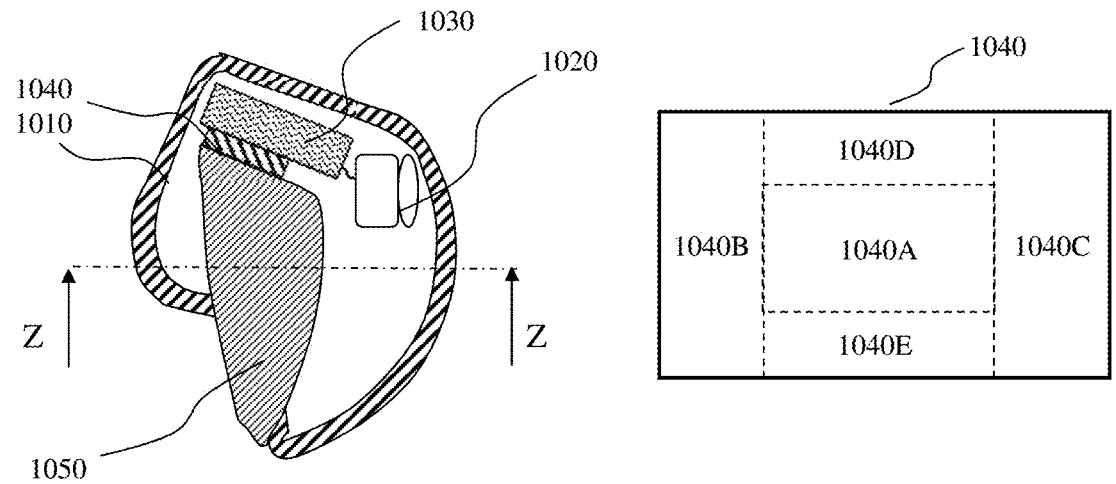
Section X-X
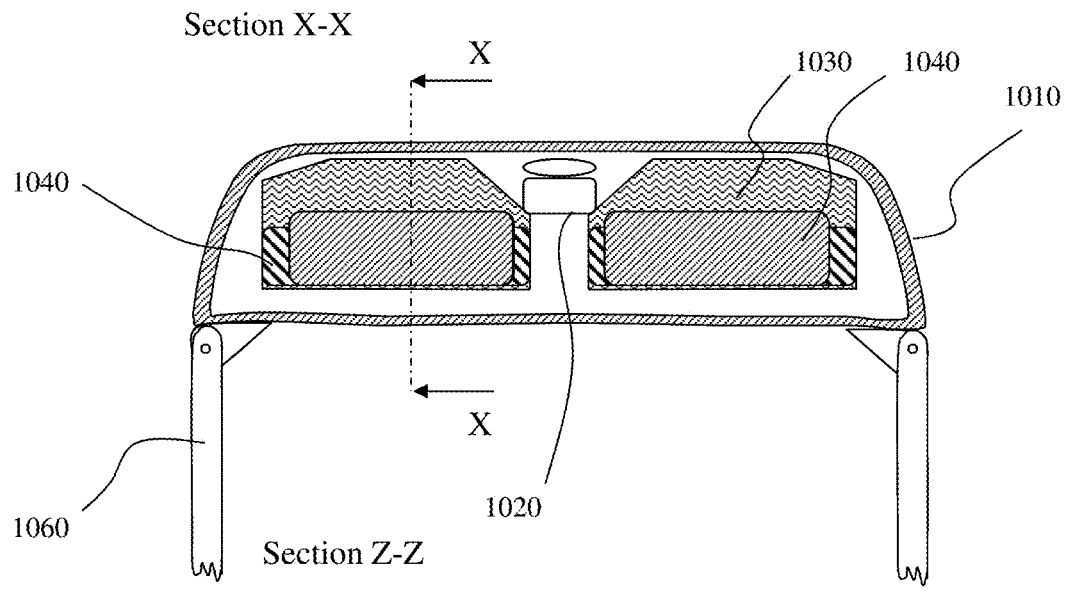
Section Z-Z

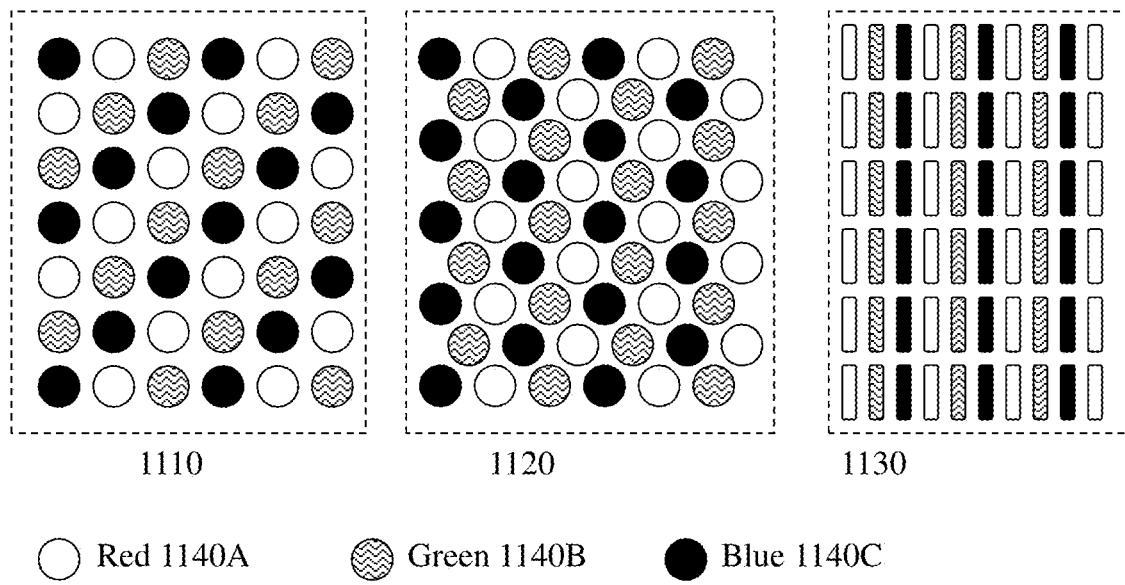
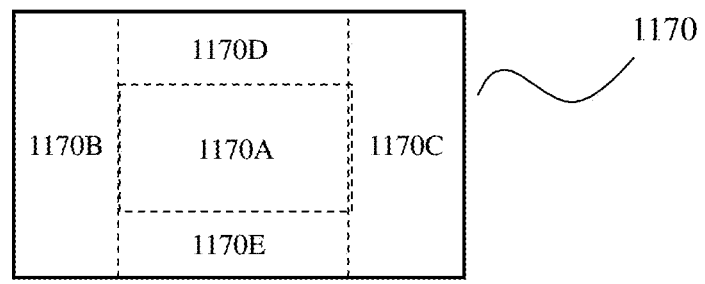
Figure 11
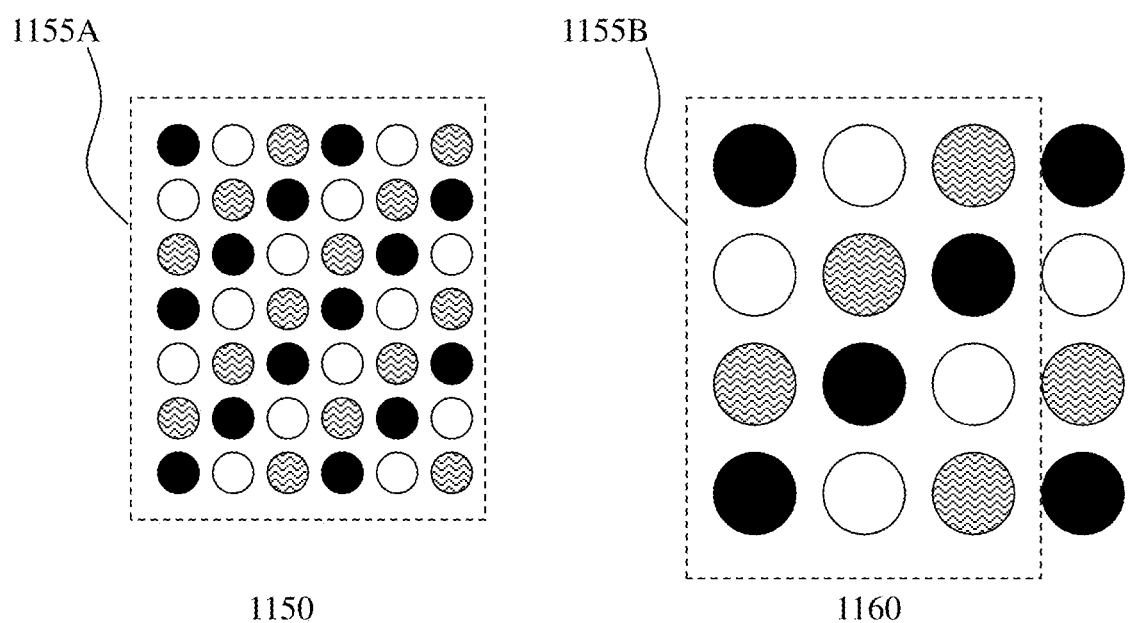

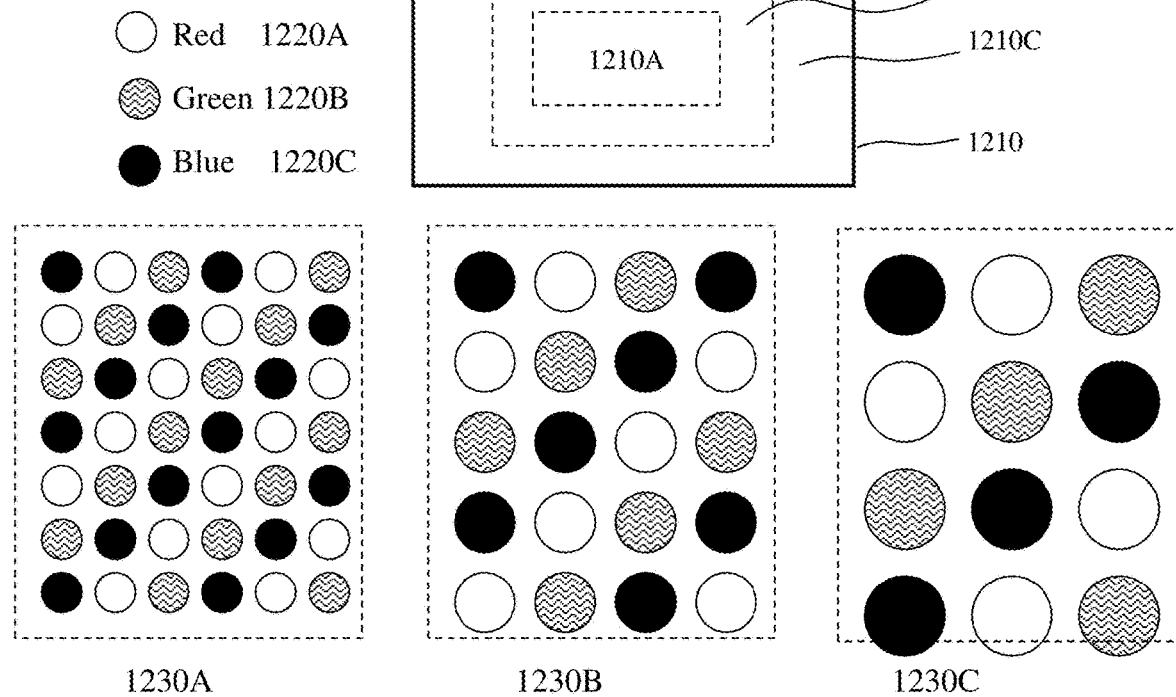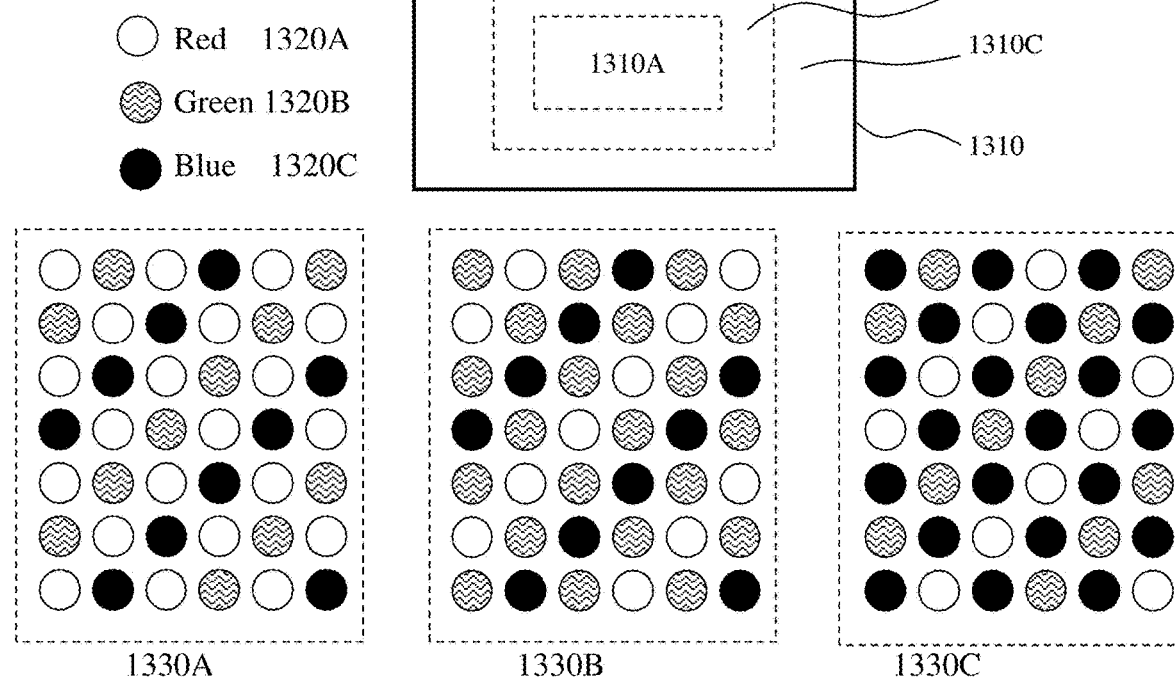

Figure 16
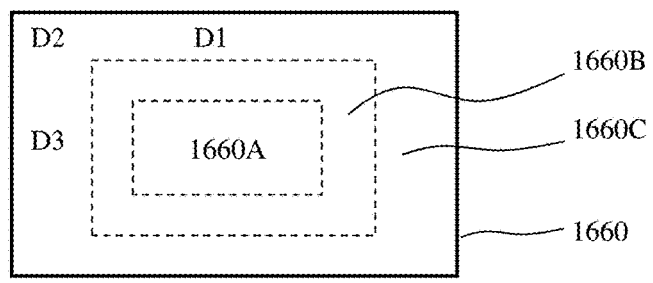
○ Red 1670A
◎ Green 1670B
● Blue 1670C
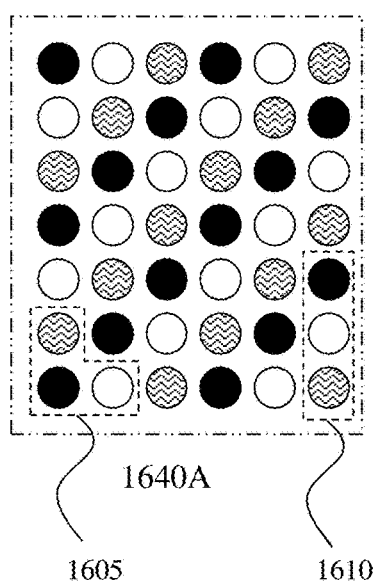
1640A
1605    1610
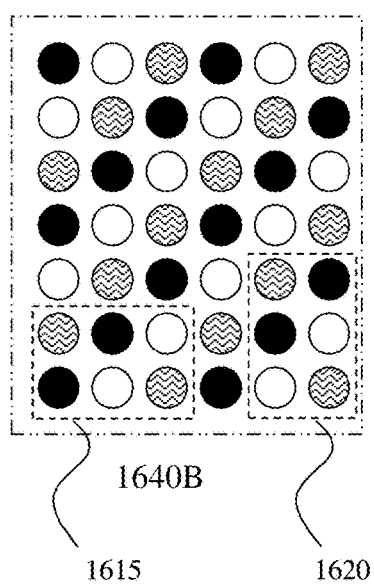
1640B
1615    1620
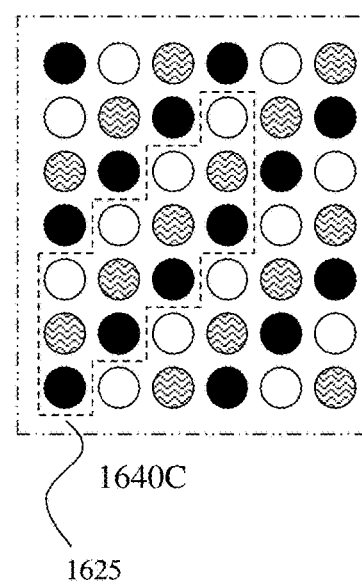
1640C
1625
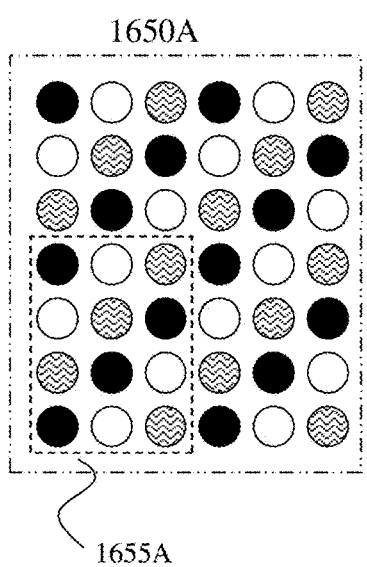
1650A
1655A
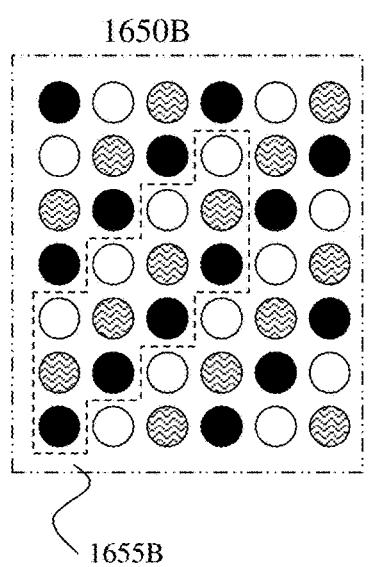
1650B
1655B
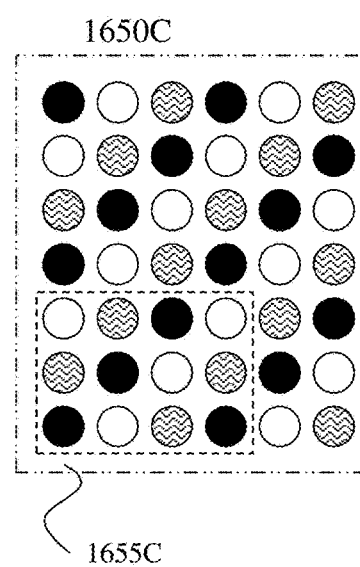
1650C
1655C

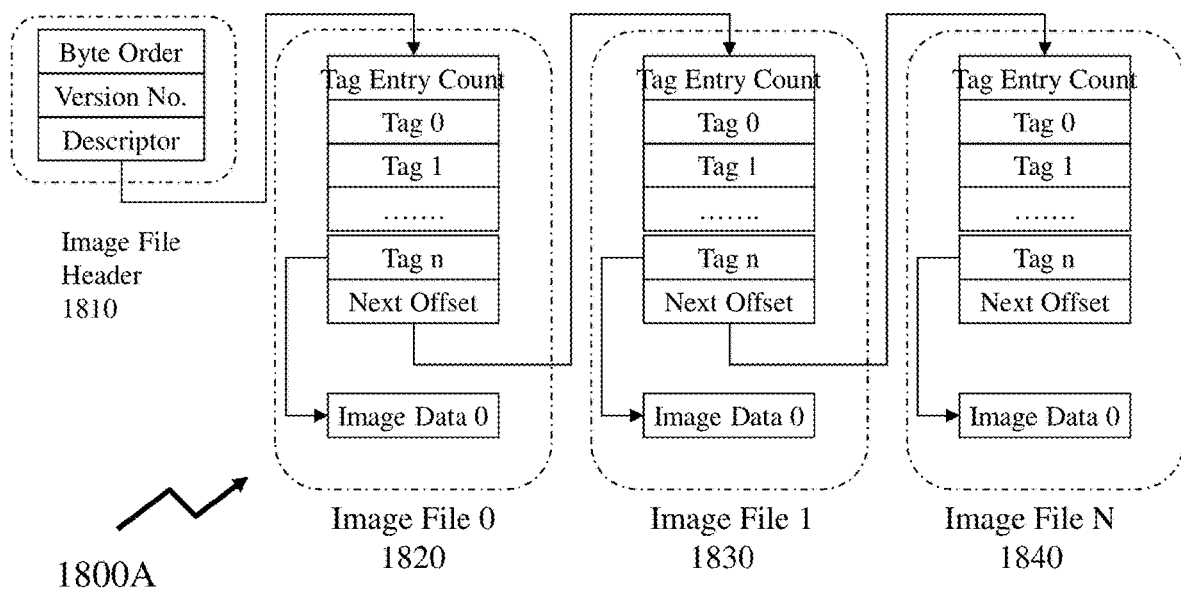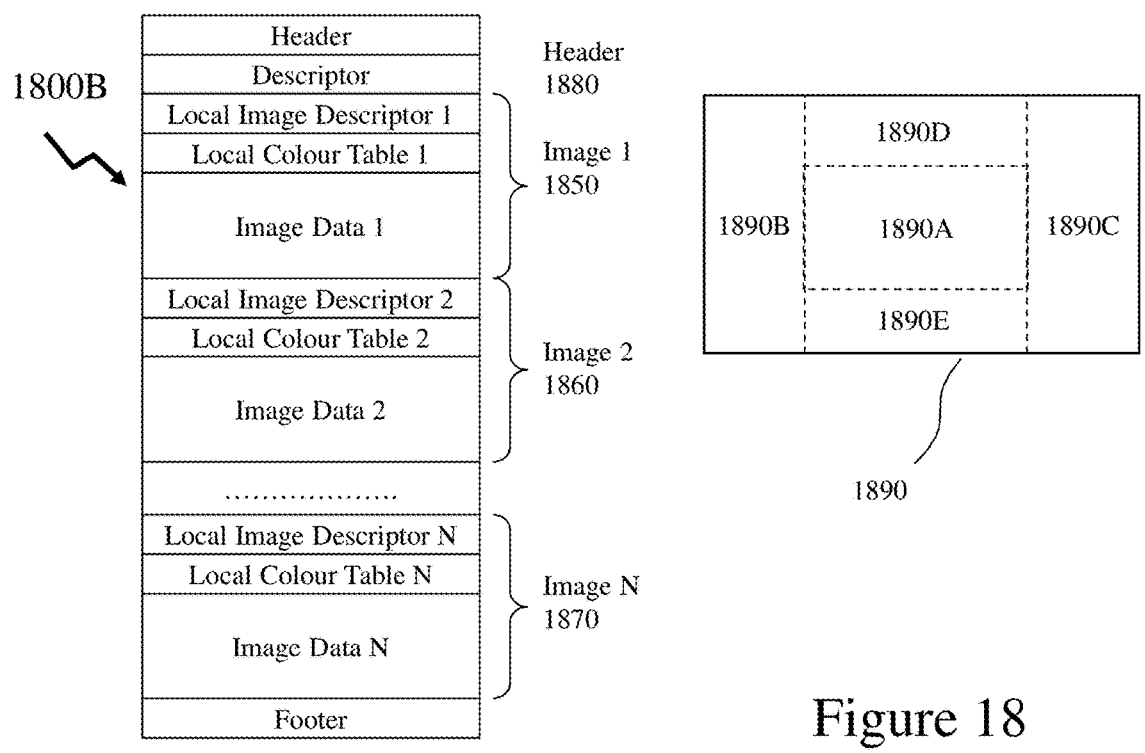
Figure 18

APPARATUS AND METHOD FOR ENHANCING HUMAN VISUAL PERFORMANCE IN A HEAD WORN VIDEO SYSTEM

CROSS-REFERENCE TO RELATED APPLICATIONS

This application claims the benefit of priority as a continuation of U.S. patent application Ser. No. 15/361,185 filed Nov. 25, 2016 entitled "Apparatus and Method for Enhancing Human Visual Performance in a Head Worn Video System" which itself claims the benefit of priority as a continuation of U.S. patent application Ser. No. 13/916,806 filed Jun. 13, 2013 entitled "Apparatus and Method for Enhancing Human Visual Performance in a Head Worn Video System" which itself claims the benefit of priority from U.S. Provisional Patent Application 61/659,128 filed Jun. 13, 2012 entitled "Apparatus and Method for Enhancing Human Visual Performance in a Head Worn Video System", the entire contents of which are included by reference.

This application claims the benefit of priority as a continuation of U.S. patent application Ser. No. 15/361,185 filed Nov. 25, 2016 entitled "Apparatus and Method for Enhancing Human Visual Performance in a Head Worn Video System" which itself claims the benefit of priority as a continuation of U.S. patent application Ser. No. 13/769,353 filed Feb. 17, 2013 entitled "Apparatus and Method for Enhancing Human Visual Performance in a Head Worn Video System" which itself claims the benefit of priority from U.S. Provisional Patent Application 61/599,996 filed Feb. 17, 2012 entitled "Apparatus and Method for Enhancing Human Visual Performance in a Head Worn Video System", the entire contents of which are included by reference.

FIELD OF THE INVENTION

The invention relates to head worn displays and more specifically to augmenting sight for people with vision loss.

BACKGROUND OF THE INVENTION

Visual impairment, or vision impairment, refers to the vision loss of an individual to such a degree as to require additional support for one or more aspects of their life. Such a significant limitation of visual capability may result from disease, trauma, congenital, and/or degenerative conditions that cannot be corrected by conventional means, such as refractive correction, such as eyeglasses or contact lenses, medication, or surgery. This degree of functional vision loss is typically defined to manifest with:
- a corrected visual acuity of less than 20/60;
- a significant central visual field defect;
- a significant peripheral field defect including bilateral visual defects or generalized contraction or constriction of field; or
- reduced peak contrast sensitivity in combination with any of the above conditions.

However, in the United States and elsewhere, more general terms such as "partially sighted", "low vision", "legally blind" and "totally blind" are used to describe individuals with visual impairments rather than quantified visual acuity. As human brain-eye combination is fundamental to how we perceive and interact with both the real and virtual worlds any degradation may have significant impact to the individual's quality of life. Whilst there are many components of the human eye and brain that impact perception, vision, stability, and control only a few dominate the path from eye to the optic nerve and therein to the brain, namely the cornea, lens, vitreous body, and retina. For age groups 12-19, 20-39, and 40-59 within the United States approximately 93%, 90%, and 92% of visual impairments can be corrected by refractive means.

Such refractive means include eyeglasses, contact lenses, and laser surgery and are normally used to correct common deficiencies, namely myopia, hyperopia, astigmatism, and presbyopia by refractive corrections through the use of concave, convex, and cylindrical lenses. However, within the age grouping 60+ this ability to correct visual impairments drops significant to approximately 60%. In fact, the ability to employ refractive corrections drops essentially continuously with increasing age as evident from Table 1 below.

TABLE 1

Dominant Vision Disorders That Cannot be Addressed with Refractive Correction

|  | 40-49 | 50-59 | 60-69 | 70-79 | 80+ |
| --- | --- | --- | --- | --- | --- |
| Intermediate Macular Degeneration | 2.0% | 3.4% | 6.4% | 12.0% | 23.6% |
| Advanced Macular Degeneration | 0.1% | 0.4% | 0.7% | 2.4% | 11.8% |
| Glaucoma | 0.7% | 1.0% | 1.8% | 3.9% | 7.7% |
| Low Vision (from all causes) | 0.2% | 0.3% | 0.9% | 3.0% | 16.7% |

|  | 40-49 | 50-64 | 65-74 | 75+ |
| --- | --- | --- | --- | --- |
| Diabetic Retinopathy | 1.4% | 3.8% | 5.8% | 5.0% |

Amongst the eye disorders that cannot be addressed through refractive correction include retinal degeneration, albinism, cataracts, glaucoma, muscular problems that result in visual disturbances, corneal disorders, diabetic retinopathy, congenital disorders, and infection. Age-related macular degeneration for example, currently affects approximately 140 million individuals globally and is projected to increase to approximately 180 million in 2020 and 208 million in 2030 (AgingEye Times "Macular Degeneration Types and Risk Factors", May 2002 and United Nations "World Population Prospects—2010 Revision", June 2011). Additionally, visual impairments can arise from brain and nerve disorders, in which case they are usually termed cortical visual impairments (CVI).

Accordingly, it would be evident that a solution to address non-refractive corrections is required. It would be further evident that the solution must address multiple disorders including, but not limited to those identified above, which manifest uniquely in each individual. For example, myopia, shortsightedness, corrected refractively with lenses is achieved through providing a concave lens of increasing strength with increasing myopia and accordingly a single generic lens blank can be machined to form concave lenses for a large number of individuals suffering from myopia or if machined to form convex lenses those suffering hyperopia. In contrast, macular degeneration will be unique to each individual in terms of the regions degenerating and their location. It would therefore be beneficial to provide a solution that corrects for visual impairments that cannot be corrected refractively that is customizable to the specific requirements of the user. Further, it would beneficial for the correction to account for varying requirements of the user according to their activities and/or context of their location as provided for example by bifocals or progressive bifocal lenses with refractive corrections.

Accordingly, the inventors have invented a head-worn or spectacle-mounted display system which derives its image source from a video camera mounted similarly, wherein the optical characteristics of the camera system, the display system and possibly even the video file format, are designed to match with the individual's visual impairment be it through retinal performance, nervous disorder, and/or higher order processing disorder. Typically, such a system would take advantage of the wearer's natural tendency to position their head/neck, and therefore the camera, so that an object of interest is positioned in the preferred location in the display. This is most commonly in the center of the display Field of View (FOV) but can be eccentrically located in some cases to avoid blind spots such as caused for example by Macular Degeneration or other visual diseases as described above.

There are several potential advantages to a system that closely matches the characteristics of human visual behavior and performance in this way. The design and selection of optical components could be optimized for very high performance near the center, most accurate regions of the human vision system, with significantly relaxed performance specifications at the periphery of the same. Alternatively, the performance may be optimized for non-central regions of the human vision system or to exploit physiological and psychological characteristics of the individual's vision system.

It would be further beneficial where the head-worn or spectacle mounted video display system presents the video to the individual's eye in a manner wherein it is intentionally altered to take advantage of the natural physiological behavior of the entire human vision system from the retinal photoreceptors and nerve cells through the occipital lobe and cerebral cortex. The video presented to the individual's eye may be modified spectrally, spatially and/or temporally to improve the individual's perception and functional vision.

Accordingly, due to the competing requirements of processing the received image content to present to the user in a format enhancing their vision and providing the image content at rates compatible with their activities and hence close to real time, it would beneficial for aspects of the system to be implementable in formats and designs allowing tradeoffs to be made. Accordingly, in some embodiments of the invention image content file formats, and the transmission of this data through the system, are modified to provide improvements for multiple competing aspects of a head-worn or spectacle mounted video display system including parameters including, but not limited to, power consumption, video frame rate, latency, and acuity etc. Likewise, elements of the optical system may be adjusted according to similar competing parameters as well as considering additional aspects including, but not limited to, cost, patient optical characteristics, and human vision characteristics.

Other aspects and features of the present invention will become apparent to those ordinarily skilled in the art upon review of the following description of specific embodiments of the invention in conjunction with the accompanying figures.

SUMMARY OF THE INVENTION

It is an object of the present invention to mitigate drawbacks in the prior art in addressing visual impediments of individuals using head worn displays.

In accordance with an embodiment of the invention there is provided a method comprising:
processing image data relating to an image with a microprocessor to separate the image data into at least two image data files of a plurality of image data files, each image data file relating to a predetermined portion of the image;
processing the image data within each image data file with the microprocessor to generate processed image data;
inserting into a header of each image data file data relating to an effect to be automatically applied to the image data by a display presenting the processed image data to the user when the data relating to the effect is present; and
transmitting to the display the image data file for display to the user.

In accordance with an embodiment of the invention there is provided a device comprising:
a digital camera for capturing an image relating to a field of view of a wearer of the device;
a microprocessor for executing an application stored within a memory associated with the microprocessor to process data received from the digital camera;
a display for displaying the data processed by the microprocessor comprising a plurality of pixels; and
a combining lens comprising a plurality of faces, a first face for receiving the output of the display, a second face disposed proximate an eye of the wearer through which the output of the display is coupled to the wearer's eye, a third face disposed opposite the second face through which the viewer views the field of view.

In accordance with an embodiment of the invention there is provided a method comprising:
providing a head mounted device comprising:
    a digital camera for capturing an image relating to a field of view of a wearer of the head mounted device;
    a display for displaying processed image data relating to the image and comprising a plurality of pixels; and
    a combining lens for overlaying the output of the display with a predetermined portion of the field of view of the wearer; and
providing a controller comprising at least a microprocessor and a memory, the controller for receiving image data from the camera and generating processed image data according to a predetermined file format and providing the processed image data to the display.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 2 shows how acuity changes as the object being viewed moves away from one's most accurate, central vision;

FIG. 3B depicts the concept that a large display viewed at a distance, or a small display with an identical number of pixels viewed at a closer distance, present an identical image to the human retina;

FIG. 3C depicts how 2400 pixels, for example, can be used to show a large field of view image with low resolution, or conversely to show higher levels of detail in a smaller field of view;

FIG. 8 depicts a head-worn or spectacle mounted video display system according to an embodiment of the invention;

FIG. 9 depicts a head-worn or spectacle mounted video display system according to an embodiment of the invention;

FIG. 10 depicts a head-worn or spectacle mounted video display system according to an embodiment of the invention;

FIG. 11 depicts standard display pixel configurations together with variable pixel dimension display according to an embodiment of the invention;

FIG. 12 depicts a variable pixel dimension display according to an embodiment of the invention;

FIG. 13 depicts a variable pixel dimension display according to an embodiment of the invention;

FIG. 16 depicts an exemplary process of providing variable pixel dimension display according to an embodiment of the invention;

FIG. 18 depicts image file data formats according to embodiments of the invention.

DETAILED DESCRIPTION

Figure 1A:
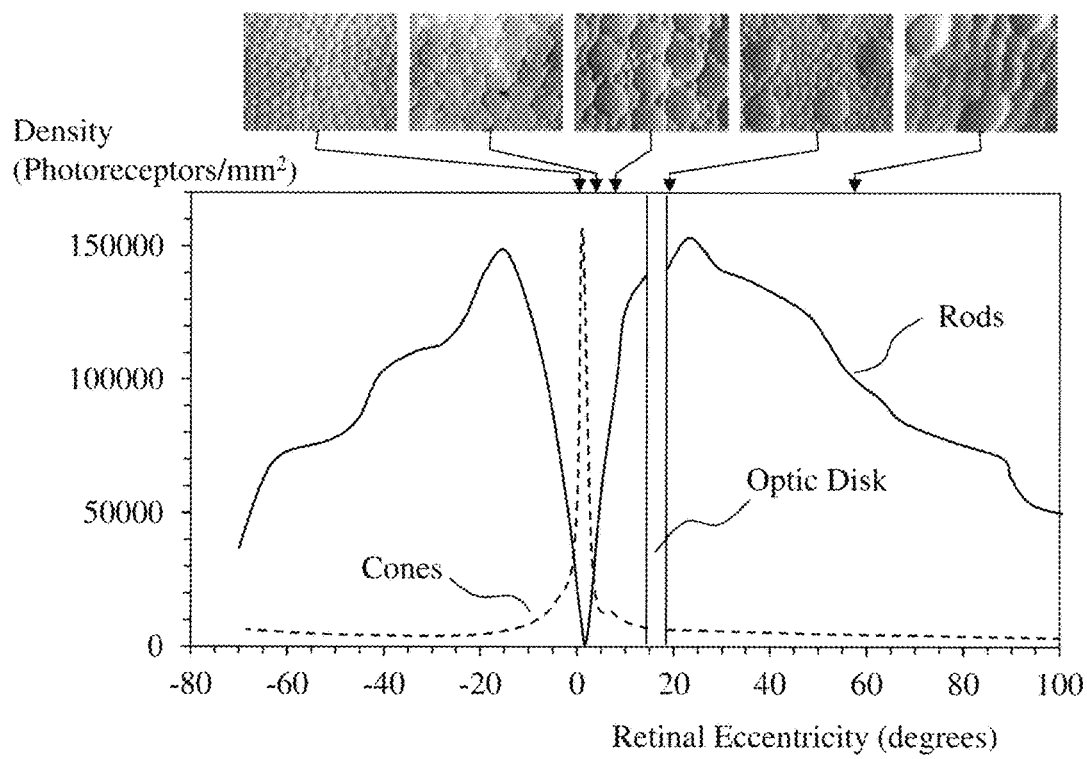
FIGS. 1A through 1D depict background information about the human vision system, including the positional density of rods and the three different cone types in the human eye, and their respective response characteristics to different wavelengths (colors) of light.

The present invention is directed to head worn displays and more specifically to augmenting sight for people with vision loss.

The ensuing description provides exemplary embodiment(s) only, and is not intended to limit the scope, applicability or configuration of the disclosure. Rather, the ensuing description of the exemplary embodiment(s) will provide those skilled in the art with an enabling description for implementing an exemplary embodiment. It being understood that various changes may be made in the function and arrangement of elements without departing from the spirit and scope as set forth in the appended claims.

A "personal electronic device" (PED) as used herein and throughout this disclosure, refers to a wireless device used for communication that requires a battery or other independent form of energy for power. This includes devices, but is not limited to, such as a cellular telephone, smartphone, personal digital assistant (PDA), portable computer, pager, portable multimedia player, portable gaming console, laptop computer, tablet computer, and an electronic reader. A "head mounted display" (HMD) as used herein and throughout this disclosure refers to a wearable device that incorporates an image capturing device and an image presentation device operating in conjunction with a microprocessor such that a predetermined portion of an image captured by the image capturing device is presented to the user on the image presentation device. Alternatively, in some cases, the source of the image for display to the wearer of the HMD may come from a remotely attached camera or any video source. The microprocessor and any associated electronics including, but not limited to, memory, user input device, gaze tracking, context determination, graphics processor, and multimedia content generator may be integrated for example with the HMD, form part of an overall assembly with the HMD, form part of the PED, or as discrete unit wirelessly connected to the HMD and/or PED.

A "user" or "patient" as used herein and through this disclosure refers to, but is not limited to, a person or individual who utilizes the HMD either as a patient requiring visual augmentation to fully or partially overcome a vision defect or as an ophthalmologist, optometrist, optician, or other vision care professional preparing a HMD for use by a patient. A "vision" defect as used herein may refer to, but is not limited, a physical defect within one or more elements of a user's eye, a defect within the optic nerve of a user's eye, a defect within the nervous system of the user, a higher order brain processing function of the user's eye, and an ocular reflex of the user.

A "file" or "image file" as used herein may refer to, but is not limited, an organized set of data relating to an image which is handled by systems and/or applications according to embodiments of the invention and may be for example temporarily stored within a memory associated with systems according to embodiments of the invention, permanently stored within memory associated with systems according to embodiments of the invention, and only stored or held within elements associated with systems according to embodiments of the invention in receiving, processing, and communicating the data between elements (i.e. associated with hardware paths or streams). According to embodiments of the invention these file formats may follow industry standards, such as for example JPEG, TIFF, and BMP, or they may be proprietary with or without the format being defined in the image file. For example, an image file may define distributions of pixels, pixel density, and colour density which are then mapped to the vision system rather than defining data for each pixel within the vision system.

The human visual system is characterized by very high visual acuity in the center of the visual field, and very poor acuity in the periphery. This is determined by the density of light sensitive photoreceptors on the human retina, the so called "rods" and "cones". There are about six million cones in the human visual system (per eye), which are heavily concentrated in the central few degrees of a person's normal 180-190 degree field of view as shown in FIG. 1A, and contribute to a person's accurate vision and color perception. There are three types of cones differentiated by length, namely short, medium and long cones. Medium and long cones are primarily concentrated to the central few degrees whilst short cones are distributed over a large retinal eccentricity. In contrast there are about 120 million rods distributed throughout the retina which contribute to peripheral performance and are particularly sensitive to light levels, sudden changes in light levels, and are very fast receptors.

Figure 1B:
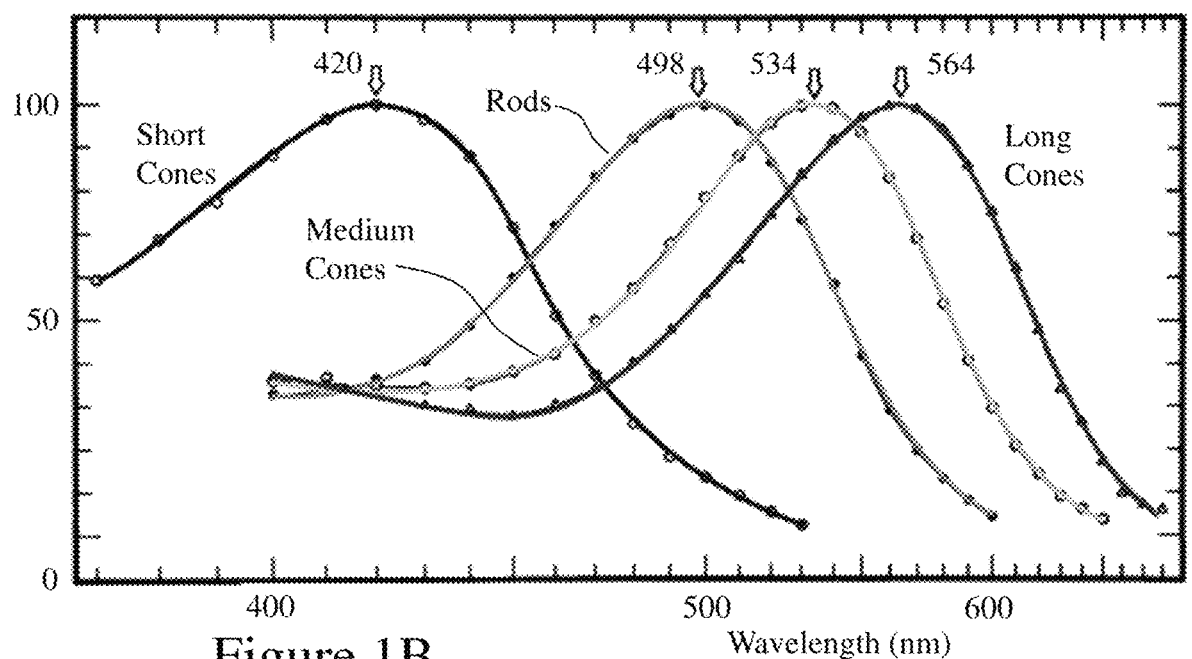
Figure 1C:
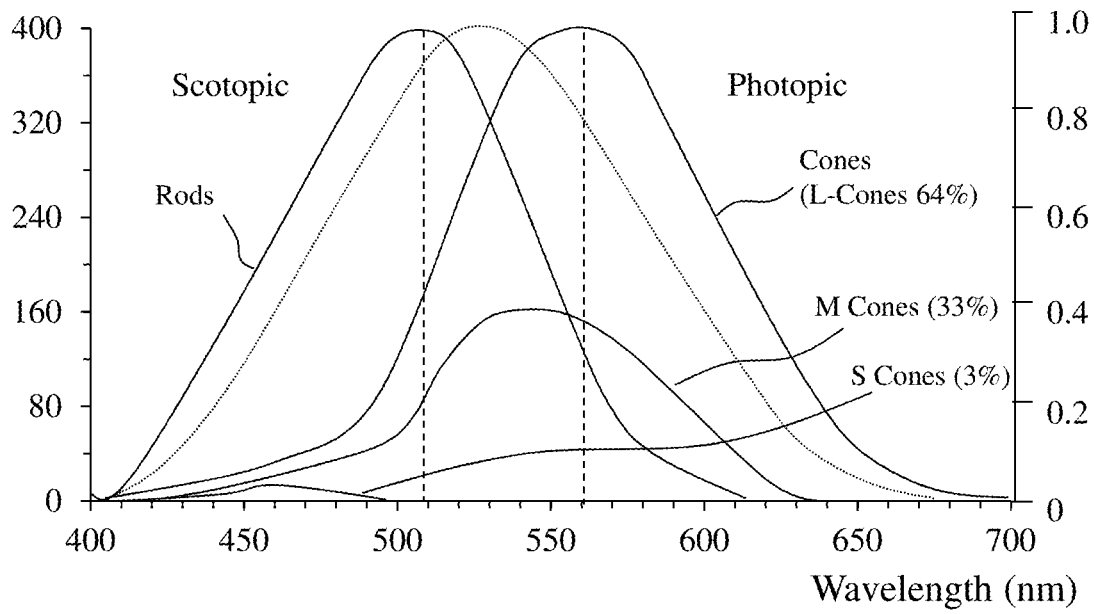
Figure 1D:
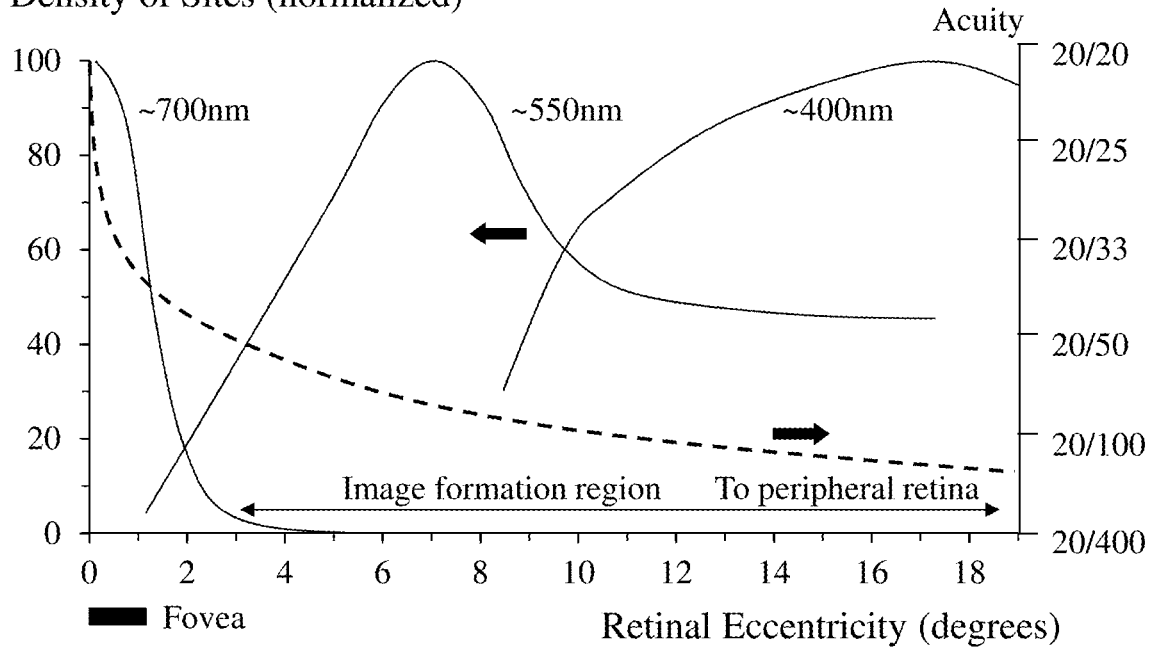

Referring to FIG. 1B the normalized absorbance of rods and cones as a function of wavelength is presented. As shown rod absorbance peaks at around 498 nm whereas short, medium, and long cones peak at around 420 nm, 534 nm, and 564 nm respectively. Accordingly, short, medium, and long cones provide blue, green and red weighted responses to the field of view of the individual. As depicted in FIG. 1C the average relative sensitivity of the rods on the left axis and three different cone types on the right hand axis cones. Peak rod sensitivity is 400 for the rods compared with 1 for the cones such that rods provide essentially monochromatic vision under very low light levels. It is also evident that the sensitivity of short, medium, and long cones also varies wherein short cones are approximately 20 times less sensitive than long cones. In a similar manner, long cones represent 64% of the cones within the human eye, medium cones 33% and short cones only 3%. The combinations of relative sensitivity, spectral sensitivities of the different cone types, and spatial distributions of the different cones types result in effective wavelength/spatial filtering of the human eye as a function of retinal eccentricity as depicted in FIG. 1D. Accordingly, as visual acuity drops from 20/20 at the fovea, approximately the first degree of retinal eccentricity to below 20/100 above 15 degrees the effective wavelength response of the human eye is red dominant at the fovea transitioning to a green dominant region between a few degrees to approximately 10 degrees followed by a blue dominant region thereafter although the rod spectral response still provides significant green sensitivity.

Figure 2:
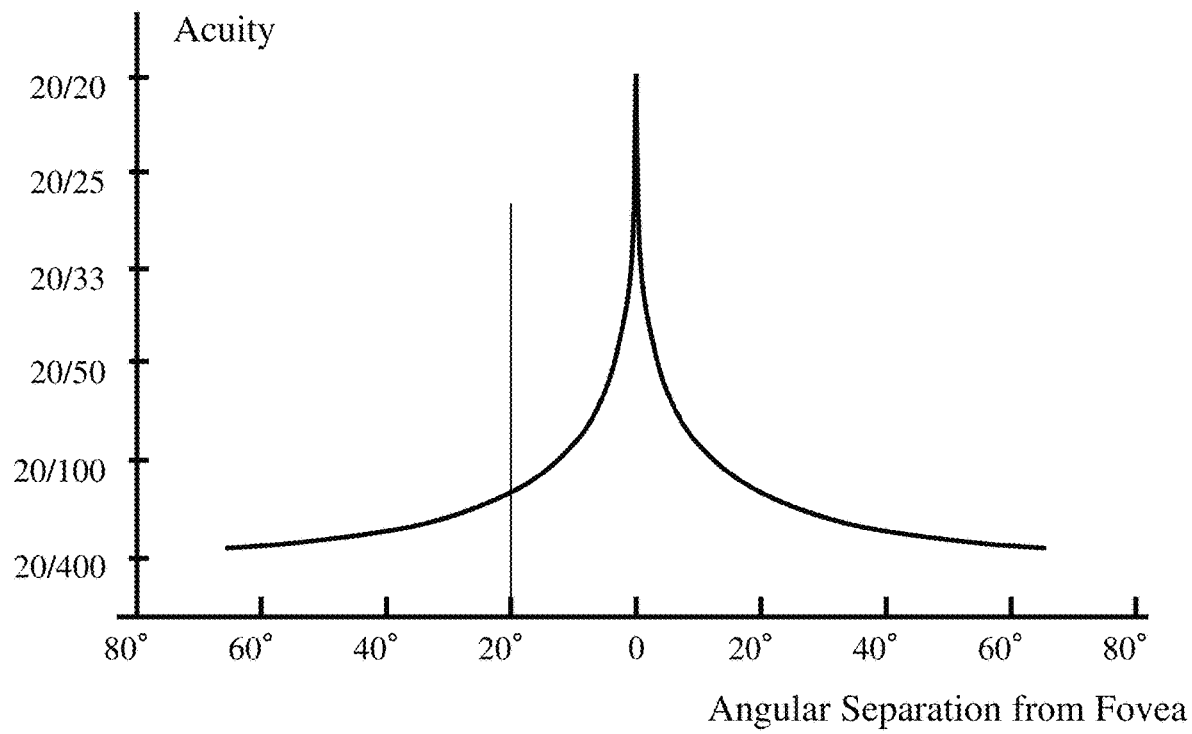
FIG. 2 depicts the acuity of the human vision system, expressed as 20/X, a nomenclature commonly understood in the field of human visual performance, and more particularly.

The corresponding visual acuity of a person with healthy eyesight is shown in FIG. 2. The common nomenclature "20/X" indicates that a person can see at 20 meters, what a healthy-sighted person could see from X meters. As shown, human vision is highly accurate in the very central 1-2 degrees of a person's visual field. 20/20 vision corresponds to a person being able to perceive an object that subtends about one minute of arc, about $1/60^{th}$ degree, on the retina in the center of their vision. At the outer periphery of a person's vision, their acuity drops significantly such that as shown in FIG. 2 outside of ±30 degrees drops to below 20/200.

Figure 3A:
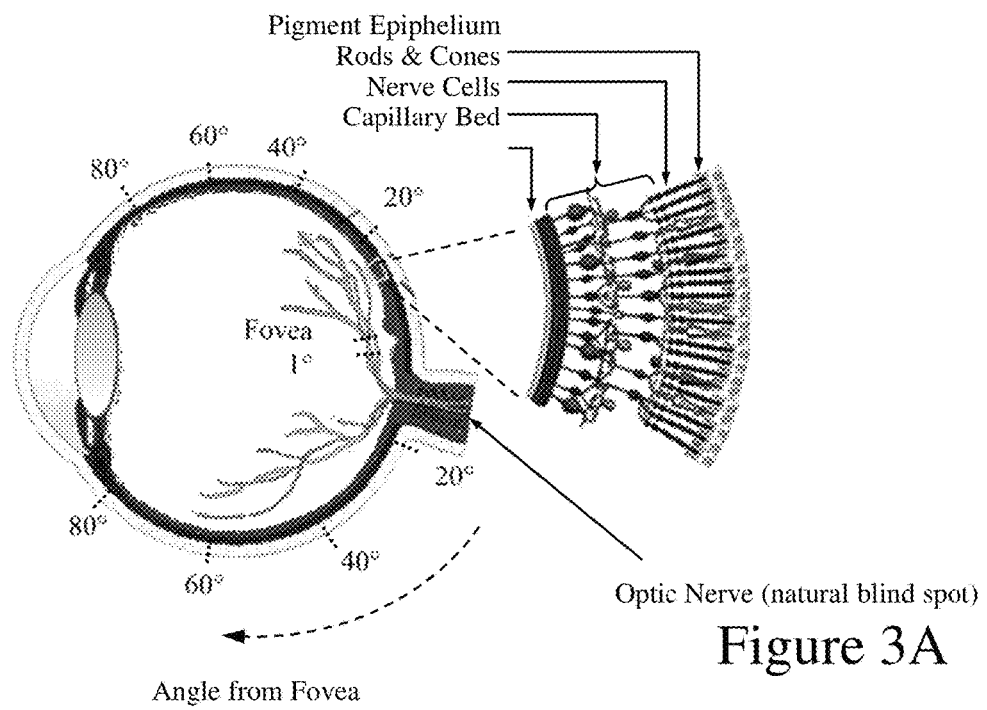
FIG. 3A is a schematic representation of the human eye.

Referring to FIG. 3A there is depicted a schematic view of the human eye, with particular detail placed upon the various types of cells that comprise the retina. Photons enter the eye via the pupil and are focused on the retina via the lens and cornea at the front of the eye. Cells in the retina are stimulated by incident photons in three ways. First, retinal photoreceptors, the rods and cones, respond to spectral qualities of the light such as wavelength and intensity. These in turn stimulate the retinal nerve cells, comprising bipolar cells, horizontal cells, ganglion cells, and amarcine cells. Although physically located in the eye, these nerve cells can be considered the most primitive part of the human brain and cortical visual function. It has also been shown that the response of photoreceptors and nerve cells improves when neighboring cells receive different spectral information. This can be considered the retina's response to spatial stimulus, that being the differences spatially between the light information incident on adjacent areas of the retina at any moment in time.

Accordingly, contrast can be defined as spectral transitions, changes in light intensity or wavelength, across a small spatial region of the retina. The sharper these transitions occur spatially, the more effectively the human vision system responds. Additionally, the eye responds to temporal changes in information, i.e. where the information stimulating photoreceptors and retinal nerve cells changes either because of object motion, head/eye motion, or other changes in the spectral/spatial information from one moment in time to the next. It is important to note that a significant portion of the human visual function takes place in the brain. In fact, retinal nerve cells can be considered an extension of the cerebral cortex and occipital lobe of the brain.

In an HMD that derives its image from a head- or spectacle-mounted video camera, the wearer's natural behavior will be to position the head and therefore the camera, such that the object of interest is positioned in the center of the display FOV. This provides a relaxing viewing posture for most individuals, adjusting the neck/head and ultimately body posture so that the eyes can relax in a centrally fixated position on the display. When the viewer perceives an object of interest in the display periphery, which is also the camera periphery, they will naturally move their head/neck/body posture so that the object is centered in the camera and therefore the display, allowing their gaze fixation to return to the most comfortably viewed area, typically the FOV center.

For wearers whose central visual field is damaged by a blind spot or visual scotoma typical of diseases such as Macular Degeneration, they may choose to position the head/neck and therefore the camera, such that the image is displayed at a preferred location that is different from the FOV center. This eccentric area of maximum visual acuity is often called a "preferred retinal loci" ("PRL") by ophthalmologists and other vision care professionals.

The acuity of human vision is maximized when the information presented to the retina provides high contrast between adjacent photoreceptors. The limit case of this is known as the retinal "yes-no-yes" response, wherein two retinal cells are stimulated and a third, situated between the first two, is not. This can be imagined as two of the horizontal bars in the "E" on an optometrist's eye chart, separated by white space of identical width, corresponding to three retinal photoreceptors. The human eye cannot discern detail that subtends smaller angles than these on the human retina. The lines and corresponding spaces for any letter on the 20/20 row of an optometrist's acuity test chart will each occupy one minute of arc, one $60^{th}$ of one degree, on a person's retina when viewed at a distance of twenty feet.

To optimize human visual performance in a head-worn or spectacle-mounted video display system, the image ought to be sufficiently "bright" to ensure as many photons as possible are carrying information to the retina. This is known as image luminance to one skilled in the art. Furthermore, improving the contrast in the image, defined as the luminance transition spatially in the image, can further improve visual performance. High contrast signals are characterized by large luminance differences, that being the difference between the brightest and darkest information in an image, across a small spatial distance. These high contrast signals are more easily processed by the human visual system, and carry the greatest information content to the human brain.

To maximize display resolution in any display system the minimum angle of resolution ("MAR") a single pixel, that being the smallest physical representation of light intensity and colour in an electronic display, subtends on the human retina ought to be about 1 minute of arc angle, corresponding to 20/20 human performance. Furthermore, because the eye can fixate on any portion of the display system, this resolution for most video systems such as televisions, portable gaming consoles, computer displays etc needs to be constant across the display. Indeed, all common image file formats and electronic image sensor and display technologies used in video systems today assume a consistent pixel size throughout the entire image area. As an example, to achieve 20/20 perceived acuity on a 4×5 aspect ratio electronic display with a 42" diagonal size, at a distance of 60" from the viewer requires 1800×1350 pixels, or approximately 2.4 million equally sized pixels. This display would subtend approximately 30 degrees (horizontally) of an individual's visual field at the 60" distance. The same pixel count would be required in a 10" display viewed at one quarter of the distance, i.e. one subtending the same angular range, or a larger display viewed from further away, again, the same subtended angle on the human retina. This is depicted in FIG. 3B.

A head-mounted display (HMD) or otherwise called head-worn, or head-borne display, uses a near-to-eye, head-mounted, or spectacle-mounted display, in which the screen is typically less than an inch in size, and special optics are designed to project its image onto the wearer's retina, giving the perception of viewing a larger display at a distance. According to embodiments of the invention this display and optics assembly projects the image to the user through the individual's eyeglasses or contact lenses which provide refractive correction wherein the display is used in conjunction with the individual's eyesight. In other embodiments the display provides the sole optical input to the individual's eye. In other embodiments a single display is used with either the left or right eye whereas in others two displays are used, one for each eye.

One of the significant challenges in developing head borne displays has been the tradeoff between display acuity, normally expressed in terms of pixel resolution or pixel size, that being the number of arc minutes subtended by a single pixel on the viewer's retina, as described above in respect of FIG. 3B, and the field of view (FOV) of the entire image, normally expressed in degrees. These two important parameters trade off; because of the physical limits of optical design, and the current limitations of electronic microdisplays. A larger FOV with the same number of display pixels results in a lower resolution image, i.e. the pixels subtend a larger area on the viewer's retina. Conversely, increasing the resolution by creating smaller pixels, without increasing the pixel count will result in a smaller, lower FOV, image. These tradeoffs are demonstrated in FIG. 3C wherein an exemplary 60×40 pixel array, i.e. a 2400 pixel image, is presented. It would be evident to one skilled in the art that typically higher pixel count displays, with increased resolution, would be employed.

Figure 4:
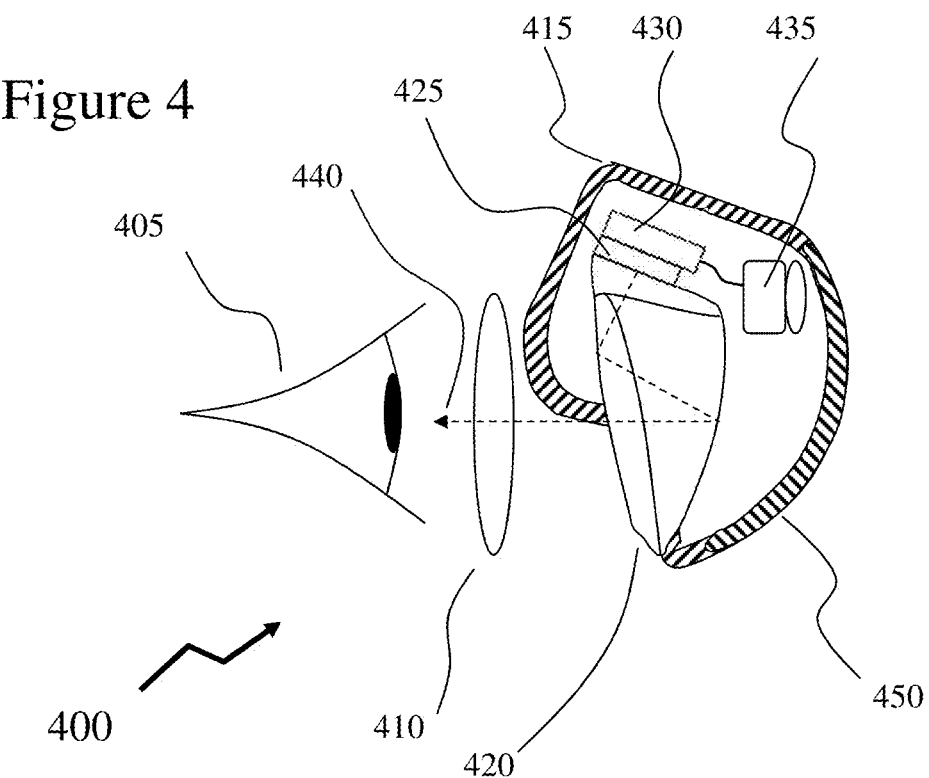
FIG. 4 depicts an optical sub-system for a head-worn or spectacle mounted video display system according to an embodiment of the invention.

Referring to FIG. 4 there is depicted a head-worn or spectacle mounted video display system 400, commonly referred to as a Head Mounted Display or HMD, according to an embodiment of the invention. Accordingly, HMD 400 is disposed in front of the viewer's eye 405 and their eyeglass lens 410. HMD 400 comprising an outer shell 415 within which are mounted a camera 435 for capturing an image of the patient's field of view (FOV) and presenting this to the patient on a display 425 via control and processing electronics 430. The content of display 425 being visually perceptible to the patient due to the multiple internal reflective path of light emitted by display 425 within HMD lens 420 and subsequent coupling to the patient's eye 405 via eyeglass lens 410 as depicted by ray path 440. According to the visual perception of the patient the "window" 450 within the outer shell 415 may be tinted, polarizing, anti-reflection coated, partially reflectively coated, or coated as in the manner of sunglasses. In some instances, the "window" 450 may be opaque such that no external light is coupled to the patient's eyes. The camera 435 being coupled via a separate optical window to "windows" 450 provided in front of the patient's eyes. For example, the camera may be centrally positioned relative to the bridge of the nose of the patient.

Figure 5:
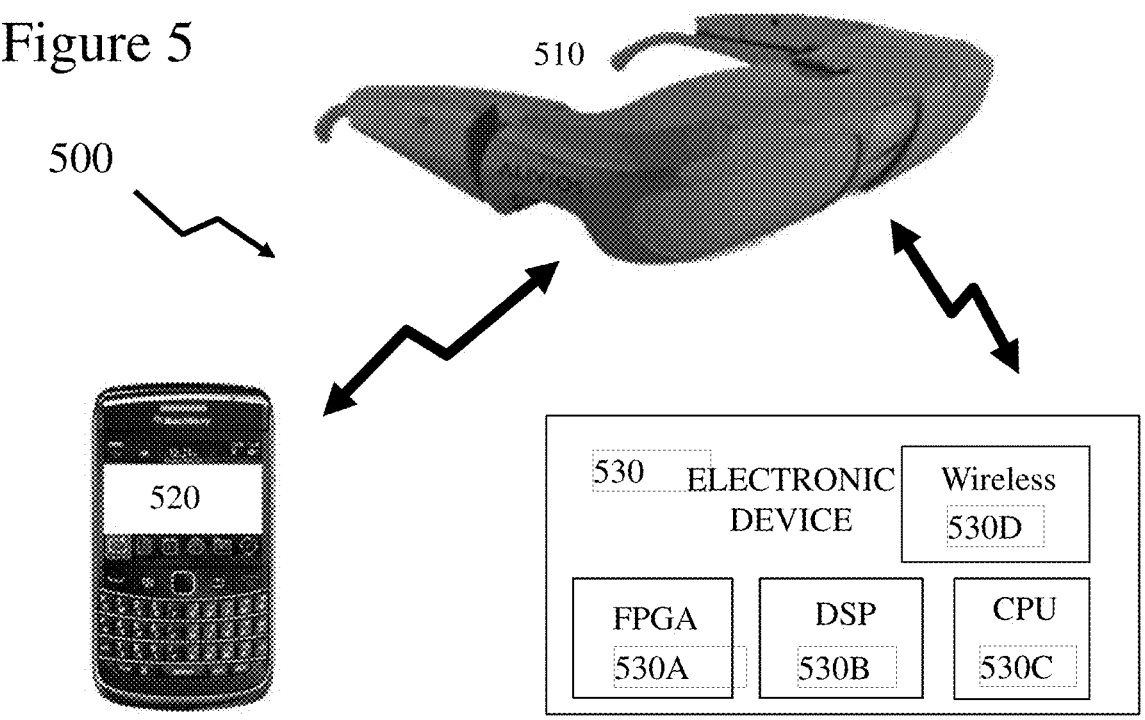
FIG. 5 depicts a head-worn or spectacle mounted video display system according to an embodiment of the invention and its connectivity to ancillary processing and control electronics.

Now referring to FIG. 5 there is depicted a HMD system 500 according to an embodiment of the invention wherein a HMD 510, such as for example eSight Eyewear by eSight Corp. of Ottawa, Canada which comprises outer shell 415, camera 435, display 425, control and processing electronics 430, and HMD lens 420 wherein the outer shell may be worn in a manner such as similar to normal eyeglasses with "windows" 450 is coupled to one or more PEDs which provide electronic processing of the image from the camera 435 thereby reducing the requirements on the control and processing electronics 430. As depicted the PEDs may be a smartphone 520 or HMD electronics 530. HMD electronics 530 comprising an FPGA 530A for memory and algorithm storage, DSP 530B for image processing and CPU 530C wherein image data received from the HMD 510 via wireless interface 530D is processed and then re-transmitted to the HMD 510 for display to the user. Smartphone 520 provides comparable functionality and may have one or more applications installed to support the graphics processing and control requirements of the HMD 510.

Accordingly, a user wearing HMD 510 or HMD 400 may be provided with enhanced vision through the acquisition of image data; it's processing to address visual defects or visual disorders of the patient, and subsequent presentation to the user through the display and lens assembly. As would be evident from FIGS. 4 and 5 such HMDs, for example HMD 400 and HMD 510 respectively, may be used with or without eyeglasses thereby combining the HMD generated content with the views own visual content received through the optical train comprising HMD lens 420 and eyeglass lens 410 or in some instances may be the sole visual content that the user receives and processes.

As depicted in FIG. 5 the HMD 510 interfaces to either electronic device 530 or smartphone 520. These computing resources may in some instances be replaced by an application specific integrated circuit (ASIC). It would be evident to one skilled in the art that smartphone 520 and electronic device 530 may be another portable electronic device (PED) including for example a cellular telephone, portable multimedia player, and portable gaming console. Alternatively, the PED may be a dedicated device for the HMD 510. As depicted within FIG. 5 elements are connected by a wireless link, this may be a wireless link operating for example according to a wireless personal area network (WPAN) or body area network (BAN) standard such as provided by IEEE 802.15 or Bluetooth for example. Optionally, the wireless link may be replaced by or augmented by a wired link which may for example be a HDMI interface although other options are also possible including, but not limited to, RS232, RS485, USB, SPC, I2C, UNI/O, Infiniband, and 1-wire.

Figure 6:
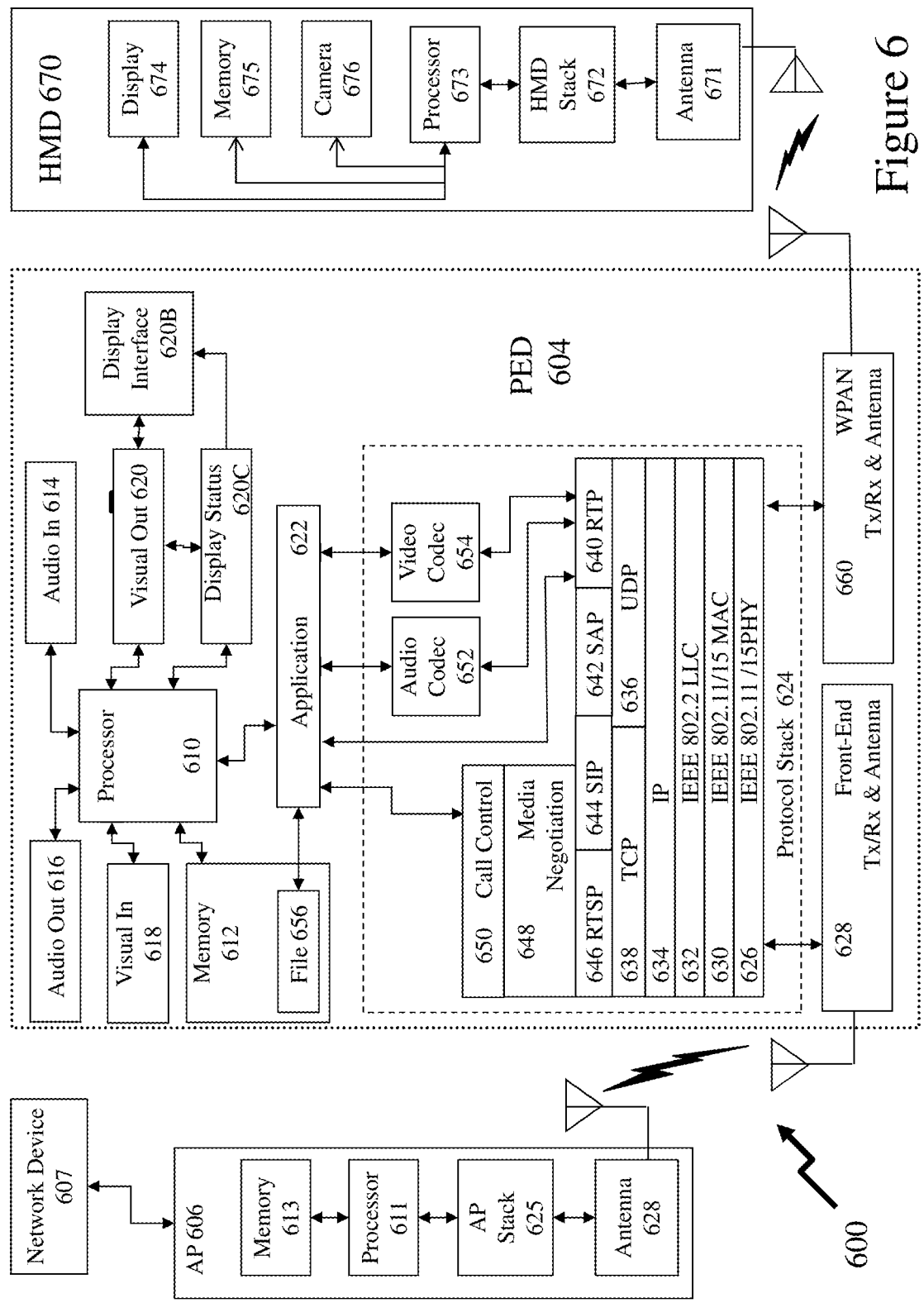
FIG. 6 depicts schematically the electronic elements of head-worn or spectacle mounted video display system and ancillary electronic devices according to an embodiment of the invention.

Referring to FIG. 6 there is depicted a portable electronic device 604 supporting an HMD according to an embodiment of the invention. Also depicted within the PED 604 is the protocol architecture as part of a simplified functional diagram of a system 600 that includes a portable electronic device (PED) 604, such as a smartphone, an access point (AP) 606, such as first Wi-Fi AP 110, and one or more network devices 607, such as communication servers, streaming media servers, and routers for example such as first and second servers 175 and 185 respectively. Network devices 607 may be coupled to AP 606 via any combination of networks, wired, wireless and/or optical communication. The PED 604 includes one or more processors 610 and a memory 612 coupled to processor(s) 610. AP 606 also includes one or more processors 611 and a memory 613 coupled to processor(s) 611. A non-exhaustive list of examples for any of processors 610 and 611 includes a central processing unit (CPU), a digital signal processor (DSP), a reduced instruction set computer (RISC), a complex instruction set computer (CISC) and the like. Furthermore, any of processors 610 and 611 may be part of application specific integrated circuits (ASICs), Field Programmable Gate Arrays (FPGAs) or may be a part of application specific standard products (ASSPs). A non-exhaustive list of examples for memories 612 and 613 includes any combination of the following semiconductor devices such as registers, latches, ROM, EEPROM, flash memory devices, non-volatile random access memory devices (NVRAM), SDRAM, DRAM, double data rate (DDR) memory devices, SRAM, universal serial bus (USB) removable memory, and the like.

PED 604 may include an audio input element 614, for example a microphone, and an audio output element 616, for example, a speaker, coupled to any of processors 610. PED 604 may include a video input element 618, for example, a video camera, and a visual output element 620, for example an LCD display, coupled to any of processors 610. The visual output element 620 is also coupled to display interface 620B and display status 620C. PED 604 includes one or more applications 622 that are typically stored in memory 612 and are executable by any combination of processors 610. PED 604 includes a protocol stack 624 and AP 606 includes a communication stack 625. Within system 600 protocol stack 624 is shown as IEEE 802.11/15 protocol stack but alternatively may exploit other protocol stacks such as an Internet Engineering Task Force (IETF) multimedia protocol stack for example. Likewise, AP stack 625 exploits a protocol stack but is not expanded for clarity. Elements of protocol stack 624 and AP stack 625 may be implemented in any combination of software, firmware and/or hardware. Protocol stack 624 includes an IEEE 802.11/15-compatible PHY module 626 that is coupled to one or more Front-End Tx/Rx & Antenna 628, an IEEE 802.11/15-compatible MAC module 630 coupled to an IEEE 802.2-compatible LLC module 632. Protocol stack 624 includes a network layer IP module 634, a transport layer User Datagram Protocol (UDP) module 636 and a transport layer Transmission Control Protocol (TCP) module 638. Also shown is WPAN Tx/Rx & Antenna 660, for example supporting IEEE 802.15.

Protocol stack 624 also includes a session layer Real Time Transport Protocol (RTP) module 640, a Session Announcement Protocol (SAP) module 642, a Session Initiation Protocol (SIP) module 644 and a Real Time Streaming Protocol (RTSP) module 646. Protocol stack 624 includes a presentation layer media negotiation module 648, a call control module 650, one or more audio codecs 652 and one or more video codecs 654. Applications 622 may be able to create maintain and/or terminate communication sessions with any of devices 607 by way of AP 606. Typically, applications 622 may activate any of the SAP, SIP, RTSP, media negotiation and call control modules for that purpose. Typically, information may propagate from the SAP, SIP, RTSP, media negotiation and call control modules to PHY module 626 through TCP module 638, IP module 634, LLC module 632 and MAC module 630.

It would be apparent to one skilled in the art that elements of the PED 604 may also be implemented within the AP 606 including but not limited to one or more elements of the protocol stack 624, including for example an IEEE 802.11-compatible PHY module, an IEEE 802.11-compatible MAC module, and an IEEE 802.2-compatible LLC module 632. The AP 606 may additionally include a network layer IP module, a transport layer User Datagram Protocol (UDP) module and a transport layer Transmission Control Protocol (TCP) module as well as a session layer Real Time Transport Protocol (RTP) module, a Session Announcement Protocol (SAP) module, a Session Initiation Protocol (SIP) module and a Real Time Streaming Protocol (RTSP) module, media negotiation module, and a call control module.

Also depicted is HMD 670 which is coupled to the PED 604 through WPAN interface between Antenna 671 and WPAN Tx/Rx & Antenna 660. Antenna 671 is connected to HMD Stack 672 and therein to processor 673. Processor 673 is coupled to camera 676, memory 675, and display 674. HMD 670 being for example system 500 described above in respect of FIG. 5. Accordingly, HMD 670 may, for example, utilize the processor 610 within PED 604 for processing functionality such that a lower power processor 673 is deployed within HMD 670 controlling acquisition of image data from camera 676 and presentation of modified image data to user via display 674 with instruction sets and some algorithms for example stored within the memory 675. It would be evident that data relating to the particular individual's visual defects may be stored within memory 612 of PED 604 and/or memory 675 of HMD 670. This information may be remotely transferred to the PED 604 and/or HMD 670 from a remote system such as an optometry system characterising the individual's visual defects via Network Device 607 and AP 606.

Accordingly, it would be evident to one skilled the art that the HMD with associated PED may accordingly download original software and/or revisions for a variety of functions including diagnostics, display image generation, and image processing algorithms as well as revised ophthalmic data relating to the individual's eye or eyes. Accordingly, it is possible to conceive of a single generic HMD being manufactured that is then configured to the individual through software and patient ophthalmic data. Optionally, the elements of the PED required for network interfacing via a wireless network (where implemented), HMD interfacing through a WPAN protocol, processor, etc may be implemented in a discrete standalone PED as opposed to exploiting a consumer PED. A PED such as described in respect of FIG. 6 allows the user to adapt the algorithms employed through selection from internal memory, to define a Region of Interest (ROI), and otherwise control the operation of the HMD through a touchscreen, touchpad, or keypad interface for example.

Further the user interface on the PED may be context aware such that the user is provided with different interfaces, software options, and configurations for example based upon factors including but not limited to cellular tower accessed, Wife/WiMAX transceiver connection, GPS location, and local associated devices. Accordingly, the HMD may be reconfigured, or situation specific information may be displayed for example, based upon the determined context of the user as determined by the PED. Optionally, the HMD may determine the context itself based upon any of the preceding techniques where such features are part of the HMD configuration as well as based upon processing the received image from the camera. For example, the HMD configuration for the user wherein the context is sitting watching television based upon processing the image from the camera may be different to that determined when the user is reading, walking, driving etc. In some instances, the determined context may be overridden by the user such as for example the HMD associates with the Bluetooth interface of the user's vehicle but in this instance the user is a passenger rather than the driver.

It would be evident to one skilled in the art that in some circumstances the user may elect to load a different image processing algorithm and/or HMD application as opposed to those provided with the HMD. For example, a third party vendor may offer an algorithm not offered by the HMD vendor or the HMD vendor may approve third party vendors to develop algorithms addressing particular requirements. For example, a third party vendor may develop an information sign set for the Japan, China etc whereas another third party vendor may provide this for Europe.

Figure 7:
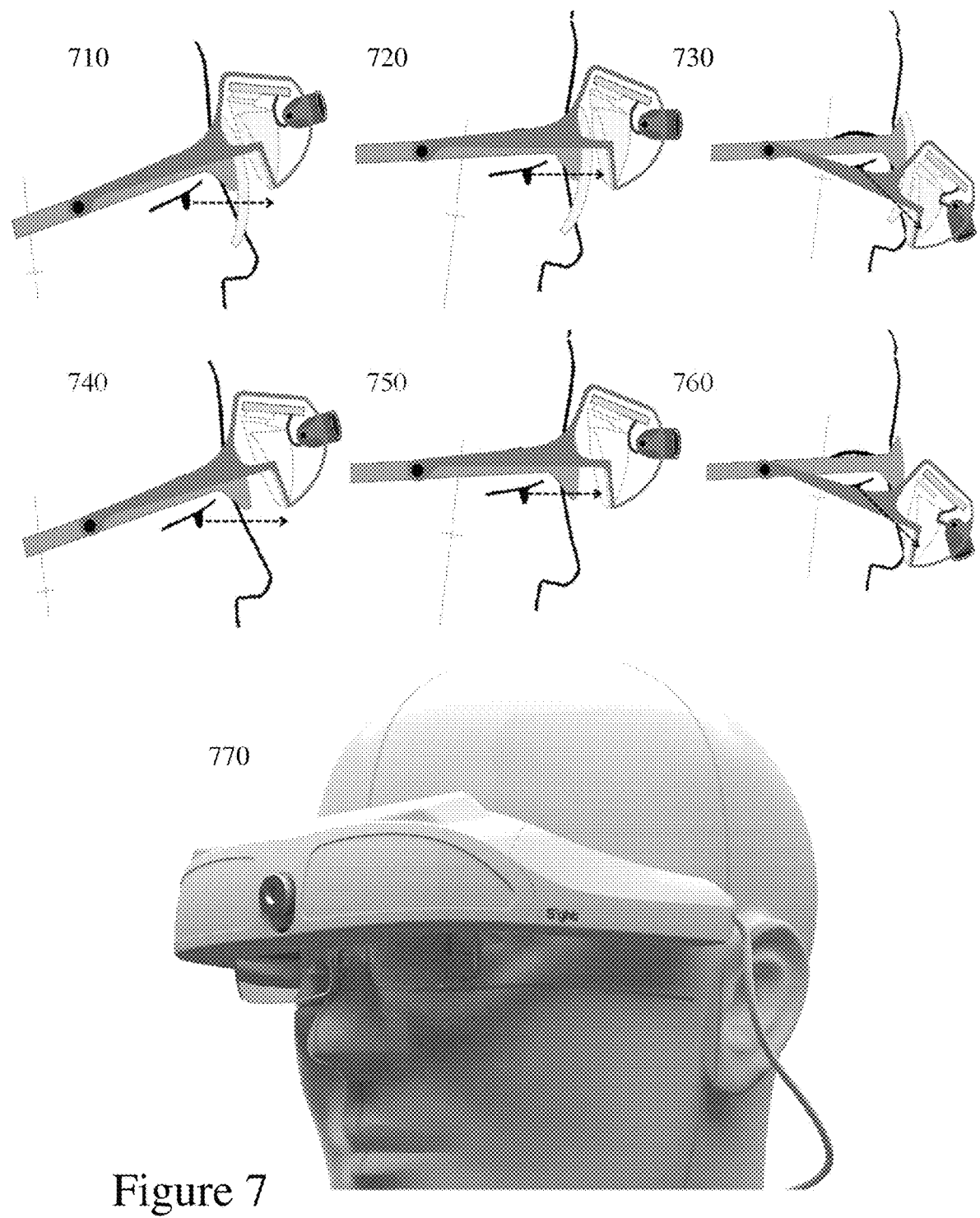
FIG. 7 depicts a head-worn or spectacle mounted video display system according to an embodiment of the invention providing multiple user engagements.

Optionally the HMD can also present visual content to the user which has been sourced from an electronic device, such as a television, computer display, multimedia player, gaming console, personal video recorder (PVR), or cable network set-top box for example. This electronic content may be transmitted wirelessly for example to the HMD directly or via a PED to which the HMD is interfaced. Alternatively, the electronic content may be sourced through a wired interface such as USB, I2C, RS485, etc as discussed above. Referring to FIG. 7 there is depicted a HMD 1370 as disclosed by R. Hilkes et al in U.S. patent application Ser. No. 13/309,717 filed Dec. 2, 2011 entitled "Apparatus and Method for a Bioptic Real Time Video System" the entire disclosure of this application is incorporated by reference herein. HMD 770 allowing a user with refractive correction lenses to view with or without the HMD 770 based upon head tilt as they engage in different activities. Accordingly, first to sixth images 710 through 760 show the different user engagement with head tilt. Within the embodiments of the invention described above and below the camera has been described as being integral to the HMD. Optionally the camera may be separate to the HMD.

In the instances that the image is the sourced from an electronic device, such as a television, computer display, multimedia player, gaming console, personal video recorder (PVR), or cable network set-top box for example then the configuration of the HMD may be common to multiple electronic devices and their "normal" world engagement or the configuration of the HMD for their "normal" world engagement and the electronic devices may be different. These differences may for example be different processing variable values for a common algorithm or it may be different algorithms.

It would be evident to one skilled in the art that the teaching of Hilkes also supports use of a HMD 770 by a user without refractive correction lenses. There being shown by first to third schematics 710 to 730 respectively in the instance of corrective lenses and fourth to sixth schematics 740 to 760 respectively without lenses. Accordingly, a user 780 working with a laptop computer 790 would typically be sitting with their head in second, third, fifth, or sixth schematic orientations wherein the HMD is engaged. In this instance the laptop computer 790 may establish a direct WPAN or wired link to the HMD 770 thereby displaying the images to the user which would otherwise be displayed on the screen of the laptop computer. In some instances, the laptop computer, due to typically increased processing resources compared to HMD 770 or a PED to which the HMD 770 is connected, may have software in execution thereon to take over processing from the HMD 770 or PED.

Now referring to FIG. 8 there is depicted a HMD 800 according to an embodiment of the invention which is displayed according to three cross-sections, two of which X-X and Y-Y are through the HMD 800 essentially in a direction perpendicular to the patient's head when wearing the HMD 800, and the third Z-Z essentially in a plane parallel to the line joining the patient's eyes. Section X-X is offset laterally to the side of one optical assembly, thereby being for example two optical assemblies one in front of each eye whereas section Y-Y is essentially through the middle of an optical assembly. Within section X-X can be seen the outer shell 810, display 840, control electronics 830, and camera 820 whereas the combination lens is shown as first section 850A which shows that section X-X cuts through the entire lens. In contrast section Y-Y shows a second section 850B and third section 850C for the combination lens wherein it is evident that the combination lens does not extend down completely in front of the patient's eye.

This may be seen in section Z-Z wherein each lens is shown as comprising two sections 860A and central portion 860B. It would therefore be evident to one skilled in the art that the combination lens, such as discussed above with HMD lens 420, therefore does not fill completely the patient's field of view rather that the central portion is absent the combination lens such that the display 840 is projected only to the peripheral portions of the patient's eye with the combination lens either comprising two lateral sections with a single portion linking them, essentially in an inverted-U design.

Such a design approach as described above in respect of FIG. 8 provides for visual information to be presented to the user with what may be considered variable fill ratio according to the portion of their visual field that does not have the combination lens, which projects the display atop the user's normal visual field, to that with the combination lens. It would be evident that optionally the combination lens may be absent the central portion such that the user is presented augmented visual content to each side of their eye.

Now referring to FIG. 9 there is depicted a HMD 900 according to an embodiment of the invention which is displayed according to three cross-sections, two of which X-X and Y-Y are through the HMD 900 essentially in a direction perpendicular to the patient's head when wearing the HMD 900, and the third Z-Z essentially in a plane parallel to the line joining the patient's eyes. Section X-X is offset laterally to the side of one optical assembly, thereby being for example two optical assemblies one in front of each eye whereas section Y-Y is essentially through the middle of an optical assembly. Within section X-X can be seen the outer shell 910, display 940, control electronics 930, and camera 920 whereas the combination lens is shown as first section 950A which shows that section X-X cuts through the entire lens. Similarly, section Y-Y shows a second section 850B for the combination lens wherein it is similarly cuts through the entire lens as opposed to the combination lens presented above in respect of FIG. 8.

This may be seen in section Z-Z wherein each lens is shown as a single element 950. Rather the display 940 is depicted as comprising two portions 940A and 940B. It would therefore be evident to one skilled in the art that the display information presented through the combination lens, such as discussed above with HMD lens 420, therefore does not fill completely the patient's field of view rather that the central portion is absent projected content. Accordingly display 940 projects only to the peripheral portions of the patient's eye. A third portion of the display 940C may be provided between the portions 940A and 940B to only project to the upper portion for the patient's vision. Such an element, would within section Z-Z be between the lens 950 and control electronics 930 and hence not visible within this section.

Accordingly, such a design approach as described above in respect of FIG. 9 provides for visual information to be presented to the user with what may be considered variable fill ratio according to the portion of their visual field that projects information to that which does not. It would be evident to one skilled in the art that alternatively a similar variable fill ratio may be obtained with a display of which different portions are used to project.

Now referring to FIG. 10 there is depicted a HMD 1000 according to an embodiment of the invention which is displayed according to two cross-sections, one being X-X through the HMD 1000 essentially in a direction perpendicular to the patient's head when wearing the HMD 1000, and the second Z-Z essentially in a plane parallel to the line joining the patient's eyes. Within section X-X can be seen the outer shell 1010, display 1040, control electronics 1030, and camera 1020 whereas the combination lens 1050 which shows that section X-X cuts through the entire lens. However, as depicted the display 1040 comprises first to fifth regions 1040A through 1040E respectively wherein as will be presented below in respect of FIGS. 11 through 13 and 16 the pixel structure and/or grouping may vary. Accordingly, for example first region 1040A may present information based upon a first pixel per inch (PPI) whereas second to fifth regions 1040B through 1040E present information based upon a second PPI. It would be evident that the PPI for each region or for different combinations of regions may be adjusted according to a variety of factors including, but not limited to, patient vision defect, cost, image processing speed, and human acuity/angular separation profile.

Referring to FIG. 11 there are presented first to third standard pixel patterns 1110 through 1130 for displays such as LED-backlit LCD, Active Matrix LCD (AMLCD), Thin-Film Transistor LCD (TFT-LCD), Plasma, and Active Matrix Organic LED (AMOLED). Accordingly, each of the first to third standard pixel patterns 1110 through 1130 comprises a regular pattern of Red (R) 1140A, Green (G) 1140B, and Blue (B) 1140C pixels which may be of a predetermined geometric shape such as circular, rectangular, square although other shapes may in principle be employed. Such displays being commonly referred to as RGB displays. In some instances, to increase display brightness a White (W) pixel may be included in the repeating pattern to form a RGBW display.

Also depicted within FIG. 11 is display 1170, such as discussed above in respect of FIG. 10, comprising a central region 1170A which employs a first display pixel pattern 1150 surrounded by first to fourth edge regions 1170B through 1170E respectively which employ a second standard pixel pattern 1160. As shown by first display segment 1155A in first display pixel pattern 1150 the pixels are disposed in accordance with first standard pixel pattern 1110 for example. Second display segment 1155B, which covers the same physical display area first display segment 1155A, is shown in second display pixel pattern 1160 shows that the pixels are disposed within the same configuration as those within the first display pixel pattern 1150 but that the pixels are now larger. Within first display segment 1155A there are 14 pixels of each colour whilst within second display segment 1155B there are 4 pixels of each colour. Accordingly, the first to fourth edge regions 1170B through 1170E present visual content at reduced PPI consistent with the reduced acuity of the user.

It would be evident to one skilled in the art that the pixels within central region 1170A may be implemented according to one of the standard patterns such as first to third standard pixel patterns 1110 through 1130 for example and the first to fourth edge regions 1170B through 1170E to have the same pattern as the central region 1170A but with larger pixels. Alternatively, the edge regions may be implemented with different pixel geometries to that of the central region and may further be implemented for example with different pixel geometries within first and second edge regions 1170B and 1170C respectively to that within third and fourth edge regions 1170C and 1170D respectively to reflect their projection onto the patient's retina. Optionally, for example if the pixels were of a linear geometry such as third standard pixel pattern 1130 then the orientation may be varied within the first to fourth edge regions 1170B through 1170E in a manner that they vary essentially radially within the display 1170.

Referring to FIG. 12 there is depicted a display 1210 comprising first to third regions 1210A through 1210C respectively comprising R, G, and B pixels 1220A through 1220C respectively in first to third pixel configurations 1230A through 1230C respectively. Accordingly, as shown within each of the first to third pixel configurations 1230A through 1230C respectively the basic configuration of the pixels remains constant but their size varies increasing from first region 1210A to third region 1210C. It would also be evident to one skilled in the art that the displays discussed above in respect of FIGS. 11 and 12 may incorporate different ratios of pixels such that for example red (R), green (G), and blue (B) pixels may for example be within the ratios such as R, G, B=[1:1:1]; R, G, B=[1:2:1]; or R, G, B=[2:3:1].

Referring to FIG. 13 there is depicted a display 1310 comprising first to third regions 1310A through 1310C respectively comprising R, G, and B pixels 1320A through 1320C respectively in first to third pixel configurations 1330A through 1330C respectively. Accordingly, as shown within each of the first to third pixel configurations 1330A through 1330C respectively the basic configuration and size of the pixels remains constant but the ratio of R, G, and B pixels 1320A through 1320C respectively varies as outlined below in Table 2. As shown in FIG. 1D the effective acuity of the human eye varies with retinal eccentricity and accordingly the ratio of R, G, and B pixels 1320A through 1320C varies radially within the display 1310. Accordingly, first to third pixel configurations 1330A through 1330C have corresponding ratios R, G, B=[21:11:10]; R,G,B=[10:21:11]; or R,G,B=[10:11:21] respectively.

TABLE 2

Distribution of R, G, B Pixels

|  | First Pixel Configuration 1330A | Second Pixel Configuration 1330B | Third Pixel Configuration 1330C |
|---|---|---|---|
| Red | 21 | 10 | 10 |
| Green | 11 | 21 | 11 |
| Blue | 10 | 11 | 21 |

Figure 14:
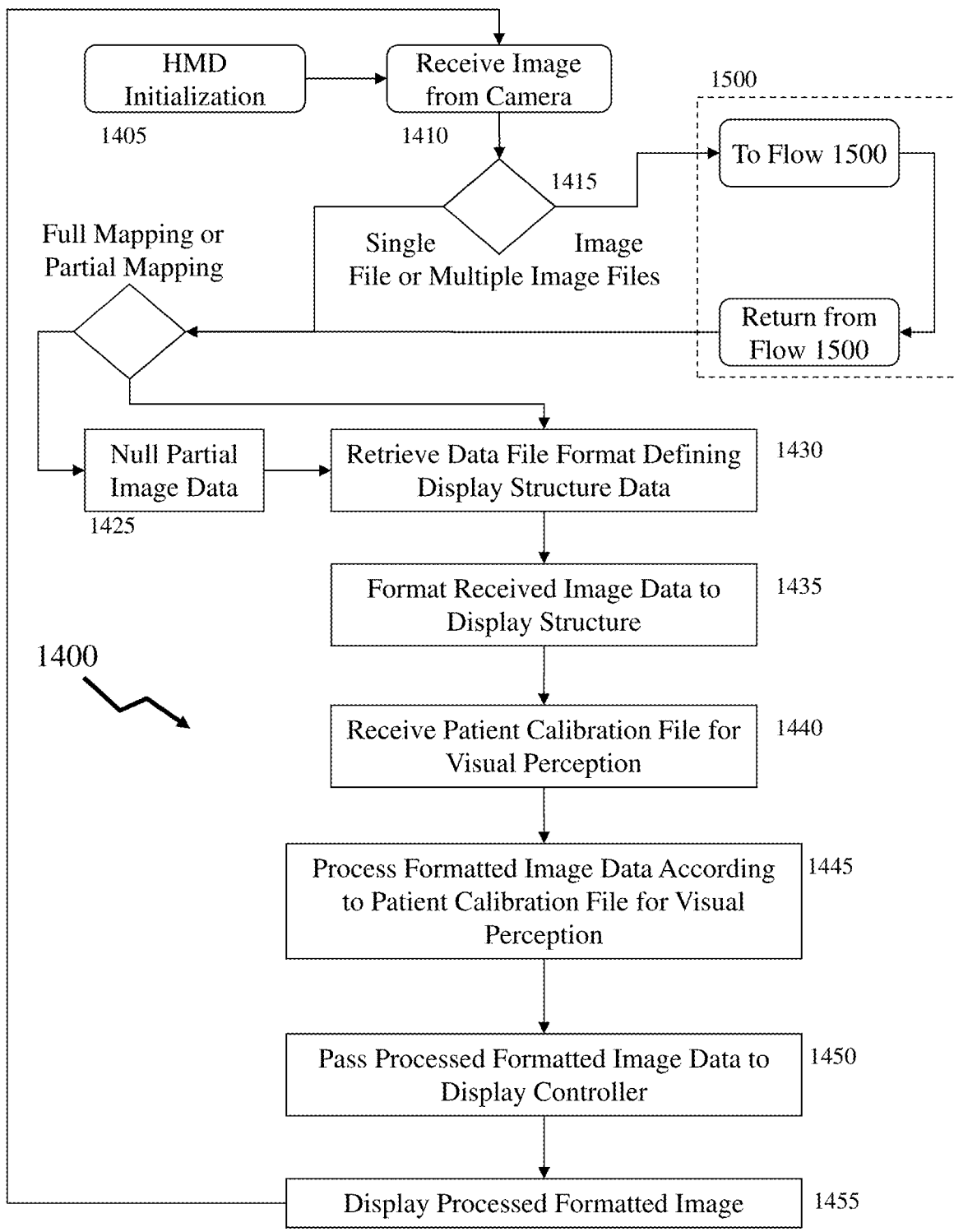
FIG. 14 depicts an exemplary process flow relating to producing an image file according to a predetermined format supporting a head-worn or spectacle mounted display according to an embodiment of the invention.

Now referring to FIG. 14 there is depicted an exemplary flow chart 1400 for a HMD according to an embodiment of the invention. As shown the process begins in step 1405 with the initialization of the HMD wherein the process proceeds to step 1410 and image data is acquired from the camera wherein the process proceeds to step 1415 wherein a determination is made as to whether the process is employing a single image file process or multiple image files. If the determination is multiple image files, then the process proceeds to process flow 1500 as described below in respect of FIG. 15 otherwise it proceeds to step 1420 wherein a determination is made as to whether full mapping of the image data is to be employed or whether partial mapping is employed. If full mapping the process proceeds to step 1430 otherwise the process proceeds similarly to step 1430 but via step 1425 wherein the portions of the image that will not be presented are nulled.

In step 1430 the data file format relating to the display structure is retrieved and then used in step 1435 to format the received image data to the display structure. For example, a display such as described supra in respect of FIG. 12 wherein the pixel count reduces in different regions may have the data file formatted to average the pixels in that region to provide the reduced image content. Alternatively, with a display such as described supra in respect of FIG. 13 the image data may be weighted spectrally to adjust the effective spectral content to the regions of the display. It would be evident that the formatting may comprise multiple such aspects based upon the display. Next in step 1440 the patient calibration data is retrieved from memory and applied in step 1445 to adjust the formatted image data to adjust the image content to reflect the visual perception deficiency of the user of the HMD.

For example, the image data may be formatted to map for a region of macular degeneration, to adjust for colour blindness, or to avoid a scotoma. Examples of such mapping are outlined within U.S. Provisional Patent Application 61/599,996 entitled "An Apparatus and Method for Enhancing Human Visual Performance in a Head Worn Video System"; U.S. patent application Ser. No. 13/371,521 entitled "An Apparatus and Method for Augmenting Sight"; U.S. patent application Ser. No. 12/891,430 entitled "Apparatus and Method for a Dynamic Region of Interest (ROI) in a Display System"; and U.S. Pat. No. 8,135,227 entitled "An Apparatus and Method for Augmenting Sight." The contents of these patent specifications in full are included within this specification by reference.

Next in step 1450 the processed formatted image data is passed to the display controller wherein the resulting data is displayed to the user in step 1455 and the process loops back to step 1410 to retrieve the next image data. Similarly, where process flow 1400 directs to process flow 1500 in step 1410 this process flow 1500 similarly returns to step 1410. Optionally, the steps within process flow 1400 may be pipelined within a processor such that for example image data relating to one image is being processed in step 1435 whilst image data relating to another image is being processed in step 1445. Such pipelining for example allowing reduced latency in presenting the modified formatted image data to the user. Nulling data that is not to be processed reduces the amount of processing required. It would be evident to one skilled in the art that alternatively the region to be processed is processed via a reduced dimension image data file that essentially crops the captured image to that portion which will be processed.

Figure 15:
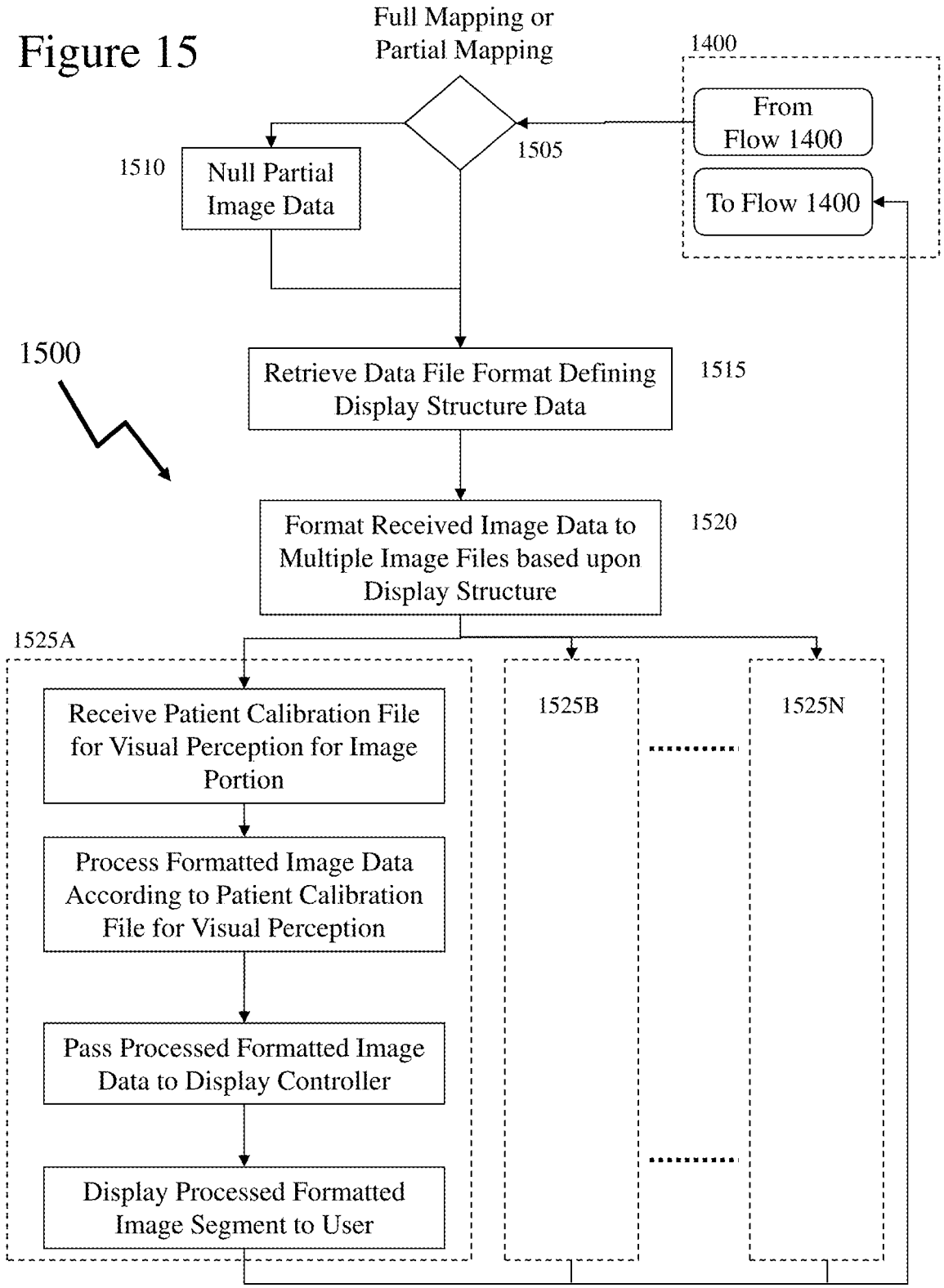
FIG. 15 depicts an exemplary process flow relating to producing an image file according to a predetermined format supporting a head-worn or spectacle mounted display according to an embodiment of the invention.

Referring to FIG. 15 there is depicted process flow 1500 as indicated above in respect of process flow 1400 in FIG. 14 this process flow is accessed where the processing will employ multiple image files derived from the captured image data. Process flow 1500 begins with step 1505 wherein the process determines whether full or partial mapping is to be performed. If full mapping is to be employed the process flow proceeds to step 1515 otherwise the process proceeds to step 1515 via step 1510 wherein the image data file is processed such that portions of the image that will not be presented are nulled. Next in step 1520 the formatted image data file is split into multiple image files in dependence upon the display structure. For example, referring to FIG. 12 the image file is split into three files representing the image content within the first to third regions 1210A to 1210C respectively. Each separate image file is then processed according to sub-process flows 1525A through 1525N wherein each sub-process flow 1525A through 1525N comprises process steps 1440 through 1455 as described in FIG. 14 with respect to process flow 1400 wherein the image file is processed according to patient calibration data and displayed to the patient using the HMD.

Referring to FIG. 16 an alternative display mapping methodology is depicted to provide effective variable pixel dimensions within a display. As described above in respect of FIGS. 11 through 13 respectively display pixel dimensions and layout may be adjusted to accommodate the visual processing characteristics of the human eye particularly where the HMD is exploiting image acquisition for the patient through peripheral and non-central vision due to scotoma or macular degeneration for example. However, non-standard LED/LCD displays may provide a cost barrier to deployment in some scenarios. Accordingly display 1660 within a HMD is structured with three regions being first to third regions 1660A through 1660C respectively wherein each comprises R, G, and B pixels 1670A through 1670C respectively.

Within first region 1660A a single image pixel may be configured as first or second pixel pattern 1605 and 1610 respectively comprising one of each of the R, G, and B pixels 1670A through 1670C respectively. Within second region 1660B a single image pixel may be configured as third or fourth pixel pattern 1615 and 1620 respectively comprising two of each of the R, G, and B pixels 1670A through 1670C respectively. Likewise, third region 1660C is composed of single image pixels which may be configured as fifth pixel pattern 1625 comprising four of each of the R, G, and B pixels 1670A through 1670C respectively. Accordingly, the first to third regions 1660A through 1660C respectively are implemented with varying image or effective pixels composed of increasing number of physical pixels, in this instance 1, 2, and 4 pixels of each of the R, G, and B pixels 1670A through 1670C respectively.

As depicted in first to third screen sections 1650A through 1650C respectively the effective image pixel varies in each from first pixel combination 1655A through second pixel combination 1655B to third pixel combination 1655C. Each of first to third screen sections 1650A through 1650C being within the third region 1660C of the display 1660 at positions D1 through D3 respectively. It would be evident that similar effective pixel images may optionally be implemented within second region 1660B of display 1660.

Figure 17:
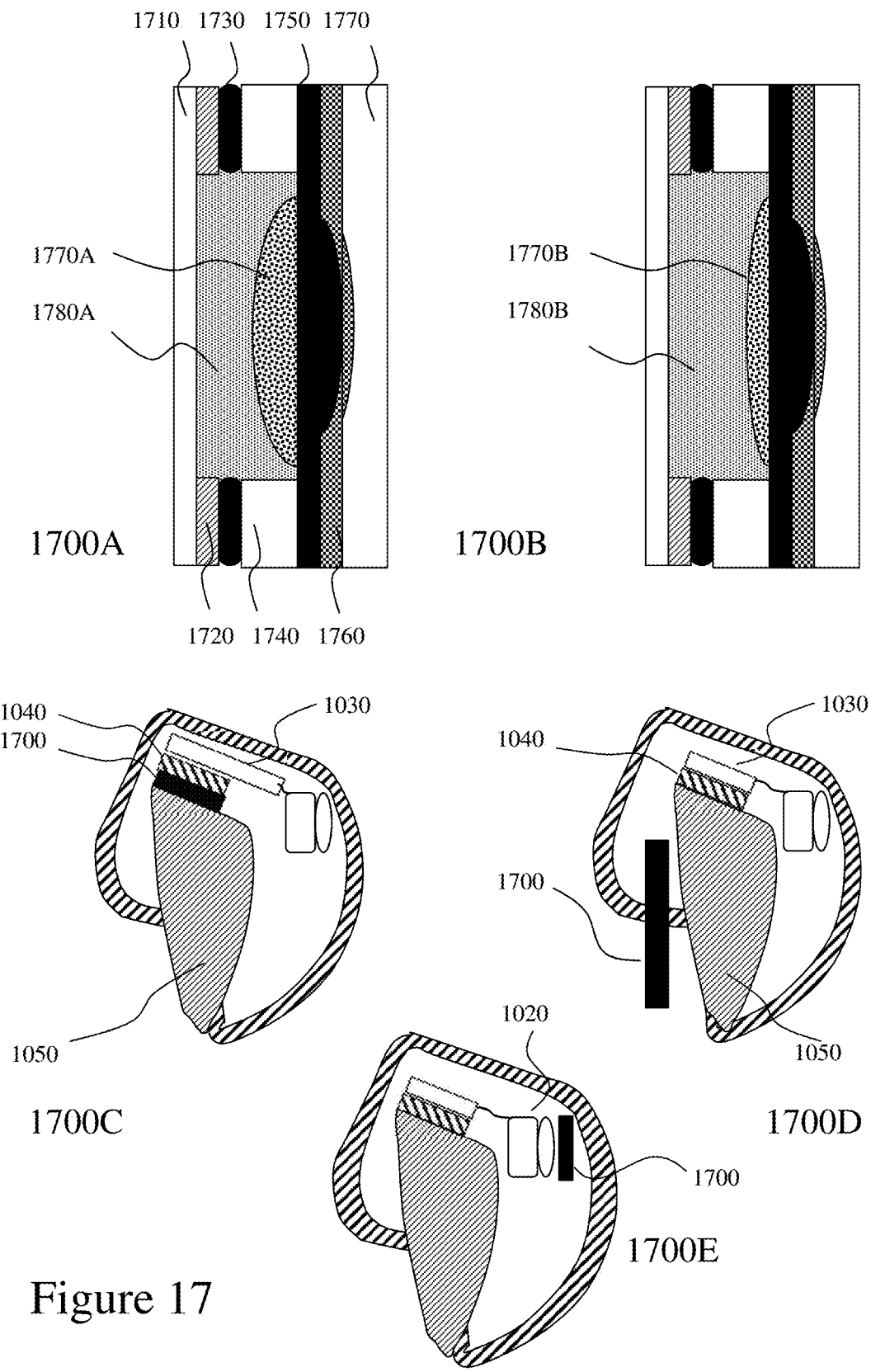
FIG. 17 depicts a head-worn or spectacle mounted display according to an embodiment of the invention employing a dynamic focal length lens within the optical assembly.
Figure 19:
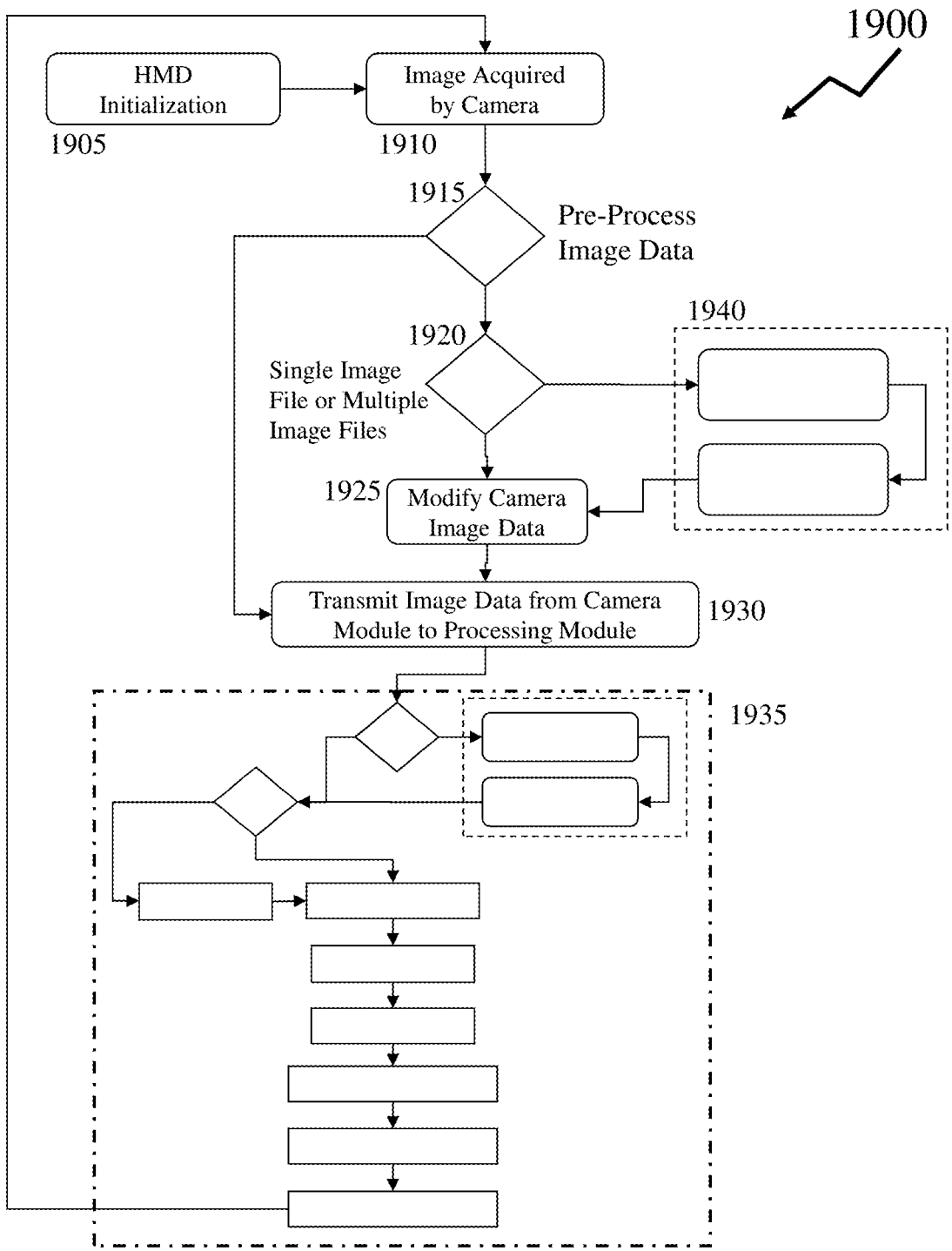
FIG. 19 depicts an exemplary process flow relating to producing an image file according to a predetermined format supporting a head-worn or spectacle mounted display according to an embodiment of the invention.

Referring to FIG. 17 there is depicted a variable lens 1700 in first and second configurations 1700A and 1700B. Variable lens 1700 comprises a mechanical assembly of base glass plate 1770 with first electrode 1760 and first insulator 1750 disposed above onto which a glass ring 1740 is positioned wherein the upper surfaces have second insulator 1730 and second electrode 1720 wherein atop the second electrode is glass cover 1710. Within the resulting chamber two non-miscible liquids are trapped. One of the liquids is based on a water solution and thus it is conductive, first liquid 1770, and the second liquid is apolar and should be non-conducting, second liquid 1780 which is typically a transparent oil. According the liquid lens 1700 is shown at two applied voltage conditions in first and second configurations 1700A and 1700B respectively. The actuation of the liquid-liquid interface is a result of electro-wetting, which enables changing the relative wettability of the two liquids by changing the applied voltage. Under these conditions the liquid-liquid interface has a spherical shape where the radius of curvature of the lens and hence its optical power varies under applied electrical control.

The liquid lens 1700 may be deployed within an HMD as depicted within first to third designs 1700C to 1700E respectively. In first design 1700C the liquid lens 1700 is disposed between display 1040 and HMD lens 1050 and controlled from the control electronics 1030 within the HMD thereby adjusting the optical path characteristics from the display to the patient's retina independent of the patient's view received from the external world through the lens 1050. In the second design 1700D the liquid lens 1700 is placed adjacent the HMD lens 1050 such that it adjusts both the image projected by the display 1040 and that coupled to the patient's retina from the external world. The liquid lens 1700 again being controlled via control electronics 1030 thereby allowing dynamic adjustment of the optical power of the liquid lens to either adjust for changes within the patient's eye, activity, or environment for example. Within the third design 1700E the liquid lens 1700 is disposed in front of the camera 1020 or may alternatively form part of the overall lens assembly for the camera 1020 such that the liquid lens 1700 provides for example for adjustment of camera angle, for example determined independence upon head orientation information, camera focusing, and image stabilization.

Within FIG. 17 the liquid lens 1700 has been described as single lens. It would be evident to one skilled in the art that for example the liquid lens 1700 may be made self-centering within the assembly by shaping elements within the liquid lens 1700 such as base glass plate 1770 with first electrode 1760 and first insulator 1750 for example. Additionally, multiple regions may be implemented within the liquid lens 1700 through patterning of the base glass plate 1770 with first electrode 1760 and first insulator 1750 for example together with multiple second electrodes 1720 thereby providing multiple lenses within a single overall liquid lens 1700 design. Additionally, adjustment of the pattern of the physical elements may allow approximations to cylindrical lenses to be formed thereby providing dynamic optical properties to be varied essentially in only one axis rather than in a circularly symmetric manner. It would also be evident that if the primary optical path is designed to be through a region between two such lens elements that the optical surface whilst approximating circular is now concave rather than convex. Further manipulation of the design may allow surfaces to approximate hyperbolic functions.

Now referring to FIG. 18 there are depicted first and second file formats 1800A and 1800B relating to storing an image file during processing by a HMD such as described above in respect of FIGS. 14 and 15. Depicted within FIG. 18 is image 1890 comprising central region 1890A and first to fourth regions 1890B through 1890B depicting the mapping of the received image to a display such as described above in respect of FIG. 10 wherein central region 1890A is to be displayed at a first PPI whereas first to fourth regions 1890B through 1890E are to be displayed at a second PPI. Optionally, the different regions may represent image regions which will be provided to the patient in accordance to embodiments of the invention including, but not limited to, those described above in respect of FIGS. 11 through 13.

First file format 1800A depicts a file format wherein image data relating to each display region is stored within a different file allowing processing and manipulation of the data within each to be undertaken in parallel such as described above in respect of FIGS. 14 and 15. Accordingly, an image file header 1810 comprises information relating to the different image files which are depicted as Image File 0 1820, Image File 1 1830 through to Image File N 1840 including a sequence of the image files. Each image file comprises a header which includes reference location of a predecessor file in the set, tag fields which that contains specific information about the bitmapped data within the image file, location of another successor file in the set, and the image data. Accordingly, tag fields within an image file may contain information relating to display characteristics such as spatial or spectral dithering such as presented within U.S. Provisional Patent Application 61/599,996 entitled "An Apparatus and Method for Enhancing Human Visual Performance in a Head Worn Video System" wherein enhanced perception of visual content may be achieved for example by dithering the image spatially or spectrally. Accordingly, rather than transmitting multiple image files to the display and its associated controller this spatial or spectral dithering for example is indicated within the image file header such that the display controller automatically applies them rather than sending sequentially two different files to provide the required dither.

Second file format 1800B represents a single file format according to an embodiment of the invention supporting presenting the image 1890 in multiple portions elements on a display. Accordingly, second file format 1800B comprises an image file header 1880 comprising information relating to the different image files which are depicted as Image 1 1850, Image 2 1860 through to Image N 1870. Each image file, such as for example Image 1 1850, comprises local image descriptor, local colour table, and image data. Local image descriptor may include for example information relating to display characteristics such as spatial or spectral dithering such as described above. Each local colour table may define weighting between R, G, and B pixels to be applied by the display controller to the image file data. Accordingly, aspects of image processing may be distributed between the HMD electronics, whether local or remote in a PED for example, with that associated with the display. For example, setting R=0 within a local colour table may set any R pixel to off irrespective of the actual data within the image data section of the associated image file.

It would be evident to one skilled in the art that exploiting image file formats such as those presented above in respect of FIG. 18 wherein the image file is broken into multiple elements provides for a mechanism for transferring portions of the image asynchronously to other portions of the image. For example, if the processing applied to the image data determines that an object is moving rapidly within one region of the display this image data file may be updated and displayed to the user without waiting for the whole image to be processed.

Now referring to FIG. 1900 there is depicted an exemplary flow chart 1900 for a HMD according to an embodiment of the invention. As shown the process begins in step 1905 with the initialization of the HMD wherein the process proceeds to step 1910 and image data is captured by an image sensor, such as for example a camera, wherein the process proceeds to step 1915 wherein a determination is made as to whether the process will pre-process the image data prior to transmitting it to a processing module. If the determination is yes, then the process proceeds to step 1920 otherwise the process proceeds to step 1930. In step 1920 a determination is made as to whether the pre-processing is to be a single image file process or multiple image files. If the determination is multiple image files then the process proceeds to process flow 1940, which may for example be equivalent to process flow 1500 as described below in respect of FIG. 15, and then to process step 1925 otherwise it proceeds to step 1925 directly. Within process step 1925 pre-processing of the image data is performed on the single or multiple image files. Such pre-processing applied to the image data from the image sensor may for example be a reduction in the dynamic range, a color correction, a removal of data relating to a predetermined portion of the user's field of view, removal of data relating to a predetermined portion of the HMD display and/or optical train between HMD display and patient's retina, and applying a predetermined mathematical process.

Within the embodiments of the invention presented above the primary consideration with respect to HMD devices has been to presenting users with visual content that has been processed in a manner allowing their visual perception to be improved relative to the unaided vision for a range of conditions which cannot be corrected with conventional refractive techniques such as eyeglasses, contact lenses, and laser eye surgery. However, it would be evident that HMD devices may also be employed by those without vision problems or those with vision defects that are corrected by refractive means in order to provide them with additional information or to adjust their vision according to an activity. For example, the HMD may provide additional information to the user such as video, images, text, multimedia content etc. associated with one or more applications being executed on a PED or other information such as directions, weather, etc. In other applications image processing of the visual image may provide automatic recognition of individuals with their name being provided to the user for example thereby allowing patients with memory retention disorders or conditions to enhance their engagements with others. Such a recognition may also provide information relating to the location of the user such as recognizing for example that they are at a bus stop for a #7 bus at Bank Street and Albert Street in Ottawa and automatically retrieve and present the estimated time of the next bus.

In other situations, the camera within the HMD may be provided to operate with a camera mounted separately to the HMD itself and may be designed to optimize performance in the near infra-red for example or under very low illumination. In other situations, the HMD presents a magnified image of the central portion of the user's FOV such that they may perform delicate work without requiring a microscope for example. There are many image modifications that can be performed on the display image to improve the visual function of the person wearing the HMD. These include, but are not limited to spectrally, spatially, partial spatial, temporally, differentially to specific objects and differentially to objects having particular characteristics.

In some instances, the visual disorder of the patient relates to the vestibulo-ocular reflex (VOR) which is a reflex eye movement that stabilizes images on the retina during head movement by producing an eye movement in the direction opposite to head movement, thus preserving the image on the center of the visual field. Since slight head movement is present all the time, the VOR is important for stabilizing vision. Patients whose VOR is impaired find it difficult to read using print, because they cannot stabilize the eyes during small head tremors. The VOR does not depend on visual input and works even in total darkness or when the eyes are closed although in the presence of light, the fixation reflex is also added to the movement. Accordingly, embodiments of the invention provide for correction of VOR impairments for patients by allowing the image displayed to the user to be adjusted for consistent visual input based upon gaze tracking.

In some patients there are no impairments to the eye physically but there are defects in the optical nerve or the visual cortex. It would be evident that where such damage results in incomplete image transfer to the brain, despite there being no retinal damage for example, that manipulation of the retinal image to compensate or address such damaged portions of the optical nerve and/or visual cortex is possible using a HMD according to embodiments of the invention.

Likewise, damage to the occipitotemporal areas of the brain can lead to patients having issues affecting the processing of shape and colour which makes perceiving and identifying objects difficult. Similarly, damage to the dorsal pathway leading to the parietal lobe may increase patient difficulties in position and spatial relationships. The most frequent causes of such brain injuries have been found to be strokes, trauma, and tumors. Accordingly, in addition to the techniques discussed above in respect of processing edges of objects, employing spatial—spectral—temporal shifts of image data on the retina the HMD may be utilised to adjust in real-time the image displayed to the user to provide partial or complete compensation. Neuro-ophthalmological uses of a HMD according to embodiments of the invention may therefore provide compensation of optical neuropathies including for example Graves' ophthalmopathy, optic neuritis, esotropia, benign and malignant orbital tumors and nerve palsy, brain tumors, neuro-degenerative processes, strokes, demyelinating disease and muscle weakness conditions such as myasthenia gravis which affects the nerve-muscle junction.

It would be evident to one skilled in the art that such compensations may include colour shifts and/or spatially adapted images which in many instances are addressed through a series of predetermined image transformations. This arises as unlike other visual defects such as macular degeneration for example, an ophthalmological examination cannot be performed to visually identify and quantify damage. Rather based upon the patient's particular visual perception disorder other effects may be utilized. In some instances, these may exploit the high visual dynamic range of regions of the retina with rods as depicted in FIG. 1C, the spectral spatial variations across the retina as described above in respect of FIG. 1D, or the spectral sensitivity differences between different cones within the same region of the retina for example. In other embodiments elements of the image may be selectively modified to address particular processing defects such that for example an inability to determine a particular shape results in the HMD adjusting those shapes within any image that contains them.

Within the embodiments of the invention described above images presented to the user have been described as having temporal variations which may be implemented at a predetermined rate. Alternatively, this rate may be varied according to one or more factors including, but not limited to, user preference, aspect of image being varied, and context. In other embodiments of the invention this rate may be varied to overcome any potential "learning to ignore" aspect of the user's visual process. Introducing variance in the effect frequency may cause the user's brain or photoreceptors to respond more effectively in the short and/or long term. With some visual disorders there may be benefit to dynamically selecting or adjusting the frequency. However, at present the absence of HMD devices allowing such effects to be applied and varied means that such effects have not been investigated. It would be evident that the rate of variation may be included within the image file data.

According to embodiments of the invention the HMD may use hardware components including image sensors, lenses, prisms and other optical components, and video displays, that mimic the inherent performance of human vision in terms of visual and cognitive spatial acuity, visual and cognitive spectral response or sensitivity to color and contrast, and visual and cognitive temporal response or sensitivity to difference in visual information from one moment in time to the next. Examples of this biomimicry could include components that have higher resolution and better color representation in the center of the field of view, and relaxed resolution and color representation, but faster refresh performance at the extremities of the field of view, thereby mimicking the natural performance characteristics of human vision.

A further embodiment of the invention could also include image file formats that are well-suited for the aforementioned biomimicing physical components. For example, a file format that does not presuppose a constant pixel size or color depth can be envisioned, wherein the resolution is much higher and color depth much greater in the center of the image than at the extremities, but the frame rate is faster at the extremities.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above and/or a combination thereof. Where embodiments of the invention have been with respect to digital or analog implementations it would be evident that optionally the alternative may be employed in many instances such as for example a general purpose microprocessor executing code for a specific filtering function may be replaced with a dedicated analog processor or that a mixed signal option may be implemented without departing from the scope of the invention.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be rearranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages and/or any combination thereof. When implemented in software, firmware, middleware, scripting language and/or microcode, the program code or code segments to perform the necessary tasks may be stored in a machine readable medium, such as a storage medium. A code segment or machine-executable instruction may represent a procedure, a function, a subprogram, a program, a routine, a subroutine, a module, a software package, a script, a class, or any combination of instructions, data structures and/or program statements. A code segment may be coupled to another code segment or a hardware circuit by passing and/or receiving information, data, arguments, parameters and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor and may vary in implementation where the memory is employed in storing software codes for subsequent execution to that when the memory is employed in executing the software codes. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels and/or various other mediums capable of storing, containing or carrying instruction(s) and/or data.

The methodologies described herein are, in one or more embodiments, performable by a machine which includes one or more processors that accept code segments containing instructions. For any of the methods described herein, when the instructions are executed by the machine, the machine performs the method. Any machine capable of executing a set of instructions (sequential or otherwise) that specify actions to be taken by that machine are included. Thus, a typical machine may be exemplified by a typical processing system that includes one or more processors. Each processor may include one or more of a CPU, a graphics-processing unit, and a programmable DSP unit. The processing system further may include a memory subsystem including main RAM and/or a static RAM, and/or ROM. A bus subsystem may be included for communicating between the components. If the processing system requires a display, such a display may be included, e.g., a liquid crystal display (LCD). If manual data entry is required, the processing system also includes an input device such as one or more of an alphanumeric input unit such as a keyboard, a pointing control device such as a mouse, and so forth.

The memory includes machine-readable code segments (e.g. software or software code) including instructions for performing, when executed by the processing system, one of more of the methods described herein. The software may reside entirely in the memory, or may also reside, completely or at least partially, within the RAM and/or within the processor during execution thereof by the computer system. Thus, the memory and the processor also constitute a system comprising machine-readable code.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system comprising:
   an electronic device comprising a first microprocessor and a first memory storing first executable instructions, the first executable instructions when executed by the first microprocessor configure the electronic device to:
   receive image data relating to an image to be presented to a patient;
   receive an indication, the indication relating to whether a full mapping or a partial mapping of the image data is to be performed;
   upon determining the indication relates to a partial mapping nulling those portions of the image data that are not to presented;
   retrieve from a second memory accessible to the electronic device a data file defining a display structure of a display upon which the image is to be presented to the user;
   format the image data into a plurality of image files in dependence upon at least the display structure defined within the data file; and
   process the plurality of image files to generate a plurality of formatted image data files; wherein
   processing the plurality of image files to generate the plurality of formatted image data files comprises for each image file of the plurality of image files:
   retrieving a patient calibration file associated with that portion of the image to which an image file of the plurality of image files relates;
   processing the image file of the plurality of image files according to the patient calibration file associated with that portion of the image to which an image file of the plurality of image files relates to generate a formatted image data file of the plurality of formatted image data files; and
   pass the formatted image data file of the plurality of formatted image data files to a display controller associated with the display upon which the image is to be presented to the user.

2. The system according to claim 1, wherein the patient calibration file relates to a characteristic of vision of the patient associated with that portion of the user's vision to which the formatted image data file relates when displayed to the patient upon the display.

3. The system according to claim 1, wherein
   processing the plurality of image files to generate the plurality of formatted image data files comprises for each image file of the plurality of image files:
   processing the image file of the plurality of image files in dependence upon a characteristic of a region of the display associated with that portion of the image to which the image file of the plurality of image files relates to generate a formatted image data file of the plurality of formatted image data files; and
   pass the formatted image data file of the plurality of formatted image data files to a display controller associated with the display upon which the image is to be presented to the user.

4. The system according to claim 1, wherein
   processing the plurality of image files to generate the plurality of formatted image data files comprises for each image file of the plurality of image files:
   processing the image file of the plurality of image files in dependence upon a characteristic of a region of an image sensor associated with that portion of the image to which the image file of the plurality of image files relates to generate a formatted image data file of the plurality of formatted image data files; and
   pass the formatted image data file of the plurality of formatted image data files to a display controller associated with the display upon which the image is to be presented to the user; wherein
   the image sensor acquired the image and generated the image data.

5. The system according to claim 1, wherein
   the data file defining the display structure of the display defines a plurality of regions of the display; and
   each region of the plurality of regions is characterised by at least one of:
   a different physical layout of pixels; and
   a different dimension of pixels.

6. The system according to claim 1, wherein
the data file defining the display structure of the display defines a plurality of regions of the display; and
each region of the plurality of regions is characterised by at least one of:
 a different weighting of a plurality of groups of pixels, each group of the plurality of groups having a predetermined wavelength range of emission;
 a different number of groups of pixels, each group of the plurality of groups having a predetermined wavelength range of emission; and
 a different physical layout of a plurality of groups of pixels, each group of the plurality of groups having a predetermined wavelength range of emission.

7. The system according to claim 1, wherein
the plurality of regions comprises either:
 apart from an inner region of the plurality of regions each other region of the plurality of regions surrounds at least one other region of the plurality of regions;
or
 an inner region;
 a first region disposed above the inner region;
 a second region disposed below the inner region;
 a third region disposed to the left of the inner region; and
 a fourth region disposed to the right of the inner region.

8. The system according to claim 1, further comprising
an imaging device comprising a second microprocessor, an imaging sensor and a second memory storing second executable instructions, the second executable instructions when executed by the second microprocessor configure the imaging device to:
 acquire data from the imaging sensor relating to the image to be presented to the user;
 pre-process the data from the imaging sensor to generate the image data; and
 transmit the image data to the electronic device.

9. The system according to claim 8, wherein
pre-processing the data from the imaging sensor comprises at least one:
 reduction of a dynamic range of the data;
 application of a color correction to the data;
 removal of a portion of the data relating to a predetermined portion of the display upon which the image is to be presented to the user;
 removal of a portion of the data relating to a predetermined portion of an optical train between the display upon which the image is to be presented to the user and the user's retina;
 application of a predetermined mathematical process.

10. The system according to claim 1, wherein
the plurality of formatted image data files comprise:
 an image header file; and
 a plurality of image files; wherein
each image file comprises:
 a header which comprises at least a reference location of a predecessor image file within the plurality of image files;
 one or more tag fields containing specific information about bitmapped data within the image file;
 a location of a successor image file within the plurality of image files; and
 a predetermined portion of the processed image data.

11. The system according to claim 1,
the first executable instructions when executed by the first microprocessor configure the electronic device to generate a file comprising the plurality of formatted image data files, wherein
each formatted image data file comprises:
 a local image descriptor;
 a local colour table, and
 image file data; wherein
each local image descriptor defines display characteristics selected from standard, spatially dithered, and spectrally dithered; and
each local colour table defines a weighting between pixels of different colours to be applied by a display controller to the image file data.

12. A system comprising:
an imaging device for acquiring an image to be presented to a user;
an electronic device comprising a first microprocessor and a first memory storing first executable instructions, the first executable instructions configuring the electronic device to:
 acquire image data from the imaging device; and
 process the image data to generate processed image data; and
a display for presenting the processed image data to the user; wherein
the first executable instructions further configure the electronic device to:
 generate a plurality of formatted image data files from the processes image data, each formatted image data file relating to a predetermined portion of the display;
 detect an object moving within a region of the image to be presented to the user; and
 update the formatted image data file relating to that region of the display associated with the region of the image within the moving object is detected independent of processing the remaining regions of the image and the remaining formatted image data files of the plurality of formatted image data files.

13. The system according to claim 12, wherein
the processed image data comprises a plurality of formatted image data files, each formatted image data file relating to a predetermined portion of the display; and
the plurality of formatted image data files are transferred asynchronously to the display.

14. A system comprising:
an electronic device comprising a first microprocessor and a first memory storing first executable instructions, the first executable instructions configuring the electronic device to:
 acquire image data from a source of image data;
 process the image data to generate processed image data; and
 at least one of:
  store the processed image data within a memory accessible to the electronic device and a display upon which the processed image data is to be displayed; and
  transmit the processed image data to the display upon which the processed image data is to be displayed; wherein
the first executable instructions further configure the electronic device to:

generate a plurality of formatted image data files from the processes image data, each formatted image data file relating to a predetermined portion of the display;
detect an object moving within a region of the image to be presented to the user; and
update the formatted image data file relating to that region of the display associated with the region of the image within the moving object is detected independent of processing the remaining regions of the image and the remaining formatted image data files of the plurality of formatted image data files.

15. The system according to claim 14, wherein
the processed image data comprises a plurality of formatted image data files, each formatted image data file relating to a predetermined portion of the display; and
the plurality of formatted image data files are transferred asynchronously to the display.

16. A system comprising:
a first display for displaying first image content to a user;
a first combining lens comprising a plurality of faces, a first face for receiving the output of the display, a second face disposed proximate an eye of the user through which the output of the display is coupled to the user's eye, and a third face disposed opposite the second face through which the user at least one of directly views a first pre-determined portion of their field of view and views the display via an optical path from the display which includes at least a reflection from the third face; and
an electronic device comprising a first microprocessor and a first memory storing first executable instructions, the first executable instructions when executed by the first microprocessor configure the electronic device to:
receive image data relating to an image to be presented to a patient;
receive an indication, the indication relating to whether a full mapping or a partial mapping of the image data is to be performed;
upon determining the indication relates to a partial mapping nulling those portions of the image data that are not to presented;
retrieve from a second memory accessible to the electronic device a data file defining a display structure of a display upon which the image is to be presented to the user;
format the image data into a plurality of image files in dependence upon at least the display structure defined within the data file; and
process the plurality of image files to generate a plurality of formatted image data files.

17. The system according to claim 16, further comprising
a second combining lens comprising a plurality of faces, a first face for receiving the output of the display, a second face disposed proximate the eye of the user through which the output of the display is coupled to the user's eye, and a third face disposed opposite the second face through which the user at least one of directly views a second pre-determined portion of their field of view and views the display via an optical path from the display which includes at least a reflection from the third face; wherein
the first combining lens is disposed laterally to one side of the user's eye at a first predetermined position;
the second combining lens is disposed laterally to the other side of the user's eye at a second predetermined position; and
the user views their field of view directly between the first combining lens and the second combining lens.

18. The system according to claim 17, wherein
the first combining lens and second combining lens are joined together at an end of each proximal their first faces.

19. The system according to claim 17, wherein
a third combining lens comprising a plurality of faces, a first face for receiving the output of the display, a second face disposed proximate the eye of the user through which the output of the display is coupled to the user's eye, and a third face disposed opposite the second face through which the user at least one of directly views a third pre-determined portion of their field of view and views the display via an optical path from the display which includes at least a reflection from the third face; wherein
the third combining lens is disposed between the first combining lens and the second combining lens.

20. The system according to claim 19, wherein
the first combining lens, the second combining lens, and the third combining lens are at least one of:
all joined together at an end of each of their first faces; and
the same lens.

21. The system according to claim 16, further comprising
a second display for displaying second image content to the user; wherein
the first display is disposed laterally to one side of the user's eye at a predetermined position;
the second display is disposed laterally to the other side of the user's eye at a second predetermined position.

22. The system according to claim 16, wherein
the first display comprises a first portion disposed laterally to one side of the user's eye, a second portion disposed laterally to the other side of the user's eye and a third portion disposed between the first portion and the second portion;
the first combining lens comprises a first portion, a second portion, and a third portion;
the first portion of the first combining lens has its portion of the first face disposed towards the first display and its portions of the second face and third face projecting down across the user's eye to a first predetermined offset relative to the first face;
the second portion of the first combining lens has its portion of the first face disposed towards the second display and its portions of the second face and third face projecting down across the user's eye to a second predetermined offset from the first face;
the third portion of the first combining lens has its portion of the first face disposed towards the third display and its portions of the second face and third face projecting down across the user's eye to a third predetermined offset from the first face.

23. A system comprising:
an electronic device comprising a first microprocessor and a first memory storing first executable instructions, the first executable instructions when executed by the first microprocessor configure the electronic device to:
receive image data relating to an image to be presented to a patient;
receive an indication, the indication relating to whether a full mapping or a partial mapping of the image data is to be performed;

upon determining the indication relates to a partial mapping nulling those portions of the image data that are not to presented;

retrieve from a second memory accessible to the electronic device a data file defining a display structure of a display upon which the image is to be presented to the user;

format the image data into a plurality of image files in dependence upon at least the display structure defined within the data file; and process the plurality of image files to generate a plurality of formatted image data files; wherein the plurality of formatted image data files each comprise:
an image header file; and
a plurality of image files; and each image file comprises:
a header which comprises at least a reference location of a predecessor image file within the plurality of image files;
tag fields containing specific information about bit-mapped data within the image file;
a location of a successor image file within the plurality of image files; and
a predetermined portion of the processed image data.

24. A system comprising:
an electronic device comprising a first microprocessor and a first memory storing first executable instructions, the first executable instructions when executed by the first microprocessor configure the electronic device to:
receive image data relating to an image to be presented to a patient;
receive an indication, the indication relating to whether a full mapping or a partial mapping of the image data is to be performed;
upon determining the indication relates to a partial mapping nulling those portions of the image data that are not to presented;
retrieve from a second memory accessible to the electronic device a data file defining a display structure of a display upon which the image is to be presented to the user;
format the image data into a plurality of image files in dependence upon at least the display structure defined within the data file; and
process the plurality of image files to generate a plurality of formatted image data files; wherein
the first executable instructions when executed by the first microprocessor further configure the electronic device to generate a file comprising the plurality of formatted image data files,
each formatted image data file comprises:
a local image descriptor;
a local colour table, and
image file data;
each local image descriptor defines display characteristics selected from standard, spatially dithered, and spectrally dithered; and
each local colour table defines a weighting between pixels of different colours to be applied by a display controller to the image file data.

* * * * *